(12) United States Patent
Tsvelikhovsky

(10) Patent No.: US 11,091,438 B2
(45) Date of Patent: Aug. 17, 2021

(54) PROCESSES FOR THE PREPARATION OF HETEROCYCLIC SCAFFOLDS FROM ALPHA ENAMINONES

(71) Applicant: Yissum Research Development Company, of The Hebrew University of Jerusalem Ltd., Jerusalem (IL)

(72) Inventor: Dmitry Tsvelikhovsky, Nof Hagalil (IL)

(73) Assignee: Yissum Research Development Company of The Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 16/495,404

(22) PCT Filed: Mar. 21, 2018

(86) PCT No.: PCT/IL2018/050327
§ 371 (c)(1),
(2) Date: Sep. 19, 2019

(87) PCT Pub. No.: WO2018/173058
PCT Pub. Date: Sep. 27, 2018

(65) Prior Publication Data
US 2020/0079738 A1    Mar. 12, 2020

Related U.S. Application Data

(60) Provisional application No. 62/474,133, filed on Mar. 21, 2017.

(51) Int. Cl.
| | | |
|---|---|---|
| C07D 215/06 | (2006.01) |
| C07D 209/54 | (2006.01) |
| C07C 225/20 | (2006.01) |
| C07D 265/36 | (2006.01) |
| C07D 333/20 | (2006.01) |
| C07D 409/06 | (2006.01) |
| C07D 413/06 | (2006.01) |

(52) U.S. Cl.
CPC .......... *C07D 215/06* (2013.01); *C07C 225/20* (2013.01); *C07D 209/54* (2013.01); *C07D 265/36* (2013.01); *C07D 333/20* (2013.01); *C07D 409/06* (2013.01); *C07D 413/06* (2013.01)

(58) Field of Classification Search
CPC .. C07D 215/06; C07D 209/54; C07D 265/36; C07D 333/20; C07D 409/06; C07D 413/06
USPC ...................................................... 546/165
See application file for complete search history.

(56) References Cited

PUBLICATIONS

David Larkin et al , Multifaceted α-Enaminone (Year: 2017).*
Brennan J. P. et al A total synthesis of+--Obscurinervidine (Year: 1985).*
Hao Shi et al . Synthesis of substitued tetrahydron-1H-carbazol-1-one and analogs via PhI(OCOCF3)2—mediated oxidative C-C bond formation. (Year: 2014).*
Cossy J. et al:—The Thermal Rearrangemnet of N-Alkyl-N-Vinylproparghlamines into 2-methylpyrroles. A new sysnthesis of Annulated[b]Pyrroles. (Year: 1996).*
Parsons et al Radical cyclisation of N-(cyclohexenyl)acrylamides: synthesis of Bicyclic N-Heterocycles. (Year: 1998).*
Arnould, J. C., et al. (1981). Reactivite photochimique des dialkylamino-2 cydohexene-2 ones et des seis d'ammonium correspondants. Tetrahedron, 37(10), 1921-1926.
Belattar, A., et al. (1992). Total synthesis of heptacydic Aspidosperma alkaloids. Part 3. Synthesis of an advanced intermediate in the synthesis of alalakine. Journal of the Chemical Society, Perkin Transactions 1, (6), 679-683.
Brennan, J. P., et al. (1985). A total synthesis of (±)-obscurinervidine. Tetrahedron letters, 26(14), 1769-1772.
Cossy, J., et al. (1996). The thermal rearrangement of N-alkyl-N-vinylpropargylamines into 2-methylpyrroles. A new synthesis of annulated [b] pyrroles. Tetrahedron letters, 37(37), 6709-6710.
Curcumelli-Rodostamo, M., et al. (1962). Lycopodium alkaloids: XII. Flabelliformine. Canadian Journal of Chemistry, 40(6), 1068-1070.
El Bialy, S. A. (2008). Efficient synthesis of (-)-y-lycorane alkaloid by two Bu3SnH-mediated radical cyclisations. Natural product research, 22(13), 1176-1188.
Greenhill, J. V. (1977). Enaminones. Chemical Society Reviews, 6(3), 277-294.
Gu, Q., et al. (2006). Synthesis of 7-substituted-5-androstene derivatives promoted by SmI2. Steroids, 71(2), 96-101.
Gu, Z. Y., et al. (2014). Palladium-catalyzed cascade reactions of isocyanides with enaminones: synthesis of 4-aminoquinoline derivatives. ACS Catalysis, 4(1), 49-52.
Hirasawa, Y., et al. (2008). Malycorins A—C, New Lycopodium Alkaloids from Lycopodium phlegmaria. Chemical and Pharmaceutical Bulletin, 56(10), 1473-1476.
International Search Report and Written Opinion issued for PCT Application No. PCT/IL2018/050327 dated Jun. 7, 2018.
Ishibashi, H., et al. (1996). Radical cyclization of chiral N-(1-cydoalken-1-yl)-a-haloacetamides: Synthesis of optically active bicyclic pyrrolidinones. Tetrahedron: Asymmetry, 7(9), 2531-2538.

(Continued)

*Primary Examiner* — Rita J Desai
(74) *Attorney, Agent, or Firm* — Mark S. Cohen; Pearl Cohen Zedek Latzer Baratz LLP

(57) ABSTRACT

The present invention provides processes for the preparation of diverse heterocyclic scaffolds from alpha-enaminone building bloc of formula (I).

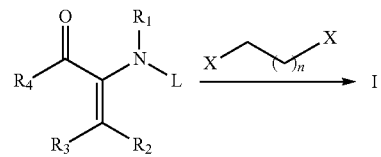

10 Claims, No Drawings

(56) References Cited

PUBLICATIONS

Kascheres, C. M. (2003). The chemistry of enaminones, diazocarbonyls and small rings: our contribution. Journal of the Brazilian Chemical Society, 14(6), 945-969.
Kasum, B., et al. (1990). Dihydroindol-7 (6H)-ones and 6, 7-Dihydropyrrolo [2, 3-c] azepine-4, 8 (1H, 5H)-dione. Australian Journal of Chemistry, 43(2), 355-365.
Krief, A., et al. (1999). Coupling of Organic Halides with Carbonyl Compounds Promoted by SmI, the Kagan Reagent. Chemical reviews, 99(3), 745-777.
Kucklander, U. (1994). Enaminones as synthones. Enamines (1994), 523-636.
Kucklander, U., et al. (1993). Protonierung von a-Keto-enaminen. Archiv der Pharmazie, 326(5), 287-290.
Lankri, D., et al. (2017). Multifaceted a-Enaminone: Adaptable Building Block for Synthesis of Heterocyclic Scaffolds Through Conceptually Distinct 1,2-, 1,3-, 1,4-, and C-O Bond Forming Annulations. The Journal of organic chemistry, 82(14), 7101-7113.
Li, H., et al. (2013). Collective synthesis of lycopodium alkaloids and tautomer locking strategy for the total synthesis of (-)-lycojapodine A. The Journal of organic chemistry, 78(3), 800-821.
Li, Y., et al. (2015). Iodine-promoted construction of polysubstituted 2, 3-dihydropyrroles from chalcones and -enamine ketones (esters). Organic letters, 17(15), 3690-3693.
Martins, F. J. C., et al. (1988). Photolysis of 2-amino-and 2-methylamino-1, 4-naphthoquinone. Tetrahedron, 44(2), 591-598.
Massa, S., et al. (1987). Potential antitumor agents. I. Synthesis of pyrroloindazole derivatives related to the pyrroloindole moieties of the antitumor antibiotic CC-1065. Ii Farmaco; edizione scientifica, 42(8), 567-574.
Molander, G. A., et al. (2002). Samarium (II) iodide-mediated intramolecular conjugate additions of a, p-unsaturated lactones. The Journal of organic chemistry, 67(11), 3861-3865.
Negri, G., et al. (2004). Recent development in preparation reactivity and biological activity of enaminoketones and enaminothiones and their utilization to prepare heterocyclic compounds. Journal of heterocyclic chemistry, 41(4), 461-491.
Parsons, A. F., et al. (1998). Radical cyclisation of N-(cydohexenyl) acrylamides: synthesis of bicyclic N-heterocycles. Tetrahedron, 54(44), 13405-13420.
Parsons, A. F., et al. (2000). Radical cyclisation reactions leading to polycyclics related to the Amaryllidaceae and Erythrina alkaloids. Tetrahedron, 56(37), 7217-7228.
Polozov, G. I., et al. (1978). Vesti Akad. Navuk BSSR Ser. Khim. Navuk, 3, 62-69.
Reddy, B. S., et al. (2013). Cu (OTf) 2-catalyzed synthesis of 2, 3-disubstituted indoles and 2, 4, 5-trisubstituted pyrroles from a-diazoketones. Organic Letters, 15(3), 464-467.
Shi, H., et al. (2014). Synthesis of substituted tetrahydron-1H-carbazol-1-one and analogs via Phi (OCOCF3) 2-mediated oxidative C-C bond formation. Tetrahedron, 70(17), 2753-2760.
Skotsch, C., et al. (1978). Die Reaktion von p-Aminovinylcarbonylverbindungen mit Diphenylcarbodiimid. Chemische Berichte, 111(5), 2003-2009.
Stork, G et al. (2001). The First Stereoselective Total Synthesis of Quinine. Journal of the American Chemical Society, 123(14), 3239-3242.
Szostak, M., et al. (2014). Cross-coupling reactions using samarium (II) iodide. Chemical Reviews, 114(11), 5959-6039.
Tobias, M. A., et al. (1970). Preparation of 2-substituted 2-cyclohexen-1-ones. The Journal of Organic Chemistry, 35(5), 1709-1711.
Trost, B. M., et al. (2012). Transition-metal-catalyzed synthesis of aspergillide B: An alkyne addition strategy. Organic Letters, 14(5), 1322-1325.
Wang, B. H., et al. (1997). Inhibition of eukaryote protein kinases by isoquinoline and oxazine alkaloids. Planta Medica, 63(06), 494-498.
Wipf, P., et al. (1993). Transmetalation reactions of organosamarium reagents. Chlorosilane-accelerated copper-catalyzed conjugate additions. The Journal of Organic Chemistry, 58(12), 3455-3459.
Yamamoto S. I., et al. (2012). Rhenium-Catalyzed Regioselective Synthesis of Multisubstituted Pyridines from p-Enamino Ketones and Alkynes via C-C Bond Cleavage. Organic Letters, 14(12), 3182-3185.

* cited by examiner

PROCESSES FOR THE PREPARATION OF HETEROCYCLIC SCAFFOLDS FROM ALPHA ENAMINONES

CROSS-REFERENCE TO RELATED APPLICATIONS

This application is a National Phase Application of PCT International Application No. PCT/IL2018/050327, International Filing Date Mar. 21,2018, claiming the benefit of U.S. Patent Application No. 62/474,133, filed Mar. 21,2017, which are hereby incorporated by reference.

TECHNOLOGICAL FIELD

The present invention provides multifaceted processes for the preparation of diverse heterocyclic scaffolds from alpha-enaminone building block.

BACKGROUND ART

References considered to be relevant as background to the presently disclosed subject matter are listed below:
1. G. Negri, C. Kascheres, A. J. Kascheres, J. Heterocyclic Chem, 2004, 41, 461;
2. J. V. Greenhill, Chem Soc. Rev., 1977, 6, 277.
3. U. Kucklander, Enarrinones as Synthones, in Enarrines, (ed. Z. Rappoport), John Wiley & Sons, Ltd, Chichester, 1994, pp. 523-637.
4. S. Yamamoto, K. Okamoto, M. Murakoso, Y. Kuninobu, K. Takai, Org. Lett., 2012, 14, 3182;
5. C. M. Kascheres, J. Braz. Chem. Soc., 2003, 14, 945;
6. Z-Y. Gu, T-H. Zhu, J-J. Cao, X-P. Xu, S-Y. Wang, S-J. Ji, ACS Catal., 2014, 4, 49.
7. B. V. S. Reddy, M. R. Reddy, Y. G. Rao, J. S. Yadav, B. Sridhar, Org. Lett., 2013, 15, 464.
8. Y. Li, H. X u, M. X ing, F. Huang, J. J ia, J. Gao, Org. Lett., 2015, 17, 3690.
9. C. Skotsch, E. Breitmaier, Chem Ber., 1978, 111, 2003.
10. J. Cossy, C. Poitevin, L. Salle, D. G. Pardo, Tetrahedron, 1996, 37, 6709;
11. B. Kasum, R. H. Prager, C. Tsopelas, Aust. J. Chem, 1990, 43, 355.
12. M. A. Tobias, J. G. Strong, R. P. Napier, J. Org. Chem, 1970, 35, 1709.
13. A. F. Parsons, D. A. Williams, Tetrahedron, 1998, 54, 13405.
14. H. Shi, T. Guo, D. Zhang-Negrerie, Y. Du, K. Zhao, Tetrahedron, 2014, 70, 2753.
15. S. A. El Bialy, Nat. Prod. Res., 2008, 22, 1176.
16. A. F. Parsons, D. A. Williams, Tetrahedron, 2000, 56, 7217.
17. A. F. Parsons, D. A. Williams, Tetrahedron, 1998, 54, 13405.
18. H. Ishibashi, Y. Fuke, T. Yamashita, M. Ikeda, Tetrahedron: Asyrmetry, 1996, 7, 2531.
19. F. J. C. Martins, A. M. Viljoen, S. J. Strydom, L. Fourie, P. L. Wessels, Tetrahedron, 1988, 44, 591.
20. S. Massa, G. Stefancich, M. Artico, F. Corelli, R. Silvestri, Farrmaco. Ed. Sci., 1987, 42, 567.
21. J. C. Arnould, J. Cossy, J. P. Pete, Tetrahedron, 1981, 37, 1921.
22. U. Kucklander, B. Schneider, Arch. Pharm, 1993, 326, 287.
23. G. I. Polozov, I. G. Tishchenko, Vesti Akad. Navuk BSSR, Ser. Khim Navuk., 1978, 3, 62.
24. H. Shi, T. Guo, D. Zhang-Negrerie, Y. Du, K. Zhao, Tetrahedron, 2014, 70, 2753.
25. M. Curcumelli-Rodostamo, D. B. MacLean, Can. J. Chem, 1962, 40, 1068.
26. H. Li, X. Wang, B. Hong, X. Lei, J. Org. Chem, 2012, 78, 800.
27. Y. Hirasawa, T. Tanaka, J. I. Kobayashi, N. Kawahara, Y. Goda, H. Morita, Chem Pharm Bull., 2008, 56, 1473.
28. B. H. Wang, Z. X. Lu, G. M. Polya, Planta med., 1997, 63, 494.
29. J. P. Brennan, J. E. Saxton, Tetrahedron Lett., 1985, 26, 1769.
30. A. B elattar, J. E. Saxton, J. Chem Soc., 1992, 1, 679.
31. G. Stork, D. Niu, A. Fujimoto, E. R. Koft, J. M. Balkovec, J. R. Tata, G. R. Dake, J. Am Chem Soc., 2001, 123, 3239.
32. B. M. Trost, M. J. Bartlett, Org. lett., 2012, 14, 1322;
33. M. Szostak, N. J. Fazakerley, D. Parmar, D. J. Procter, Chem rev., 2014, 114, 5959.
34. D. J. Jr. St. J ean, G. A. Molander, J. Org. Chem, 2002, 67, 3861.
35. A. Krief, A. M. Laval, Chem rev., 1999, 99, 745.
36. Q. Gu, Y. H. Zheng, Y. C. Li, Steroids, 2006, 71, 96.
37. P. Wipf, S. V enkatraman, J. Org. Chem, 1993, 58, 3455.

Acknowledgement of the above references herein is not to be inferred as meaning that these are in any way relevant to the patentability of the presently disclosed subject matter.

BACKGROUND

Enaminoketones have attracted increased interest, particularly cyclic-β-enaminones, which are known as important intermediates and have proven to be versatile building blocks for the synthesis of various heterocycles and natural products. The N- and f-positions are their most reactive sites. Acting as bisnucleophiles, β-enaminones are suitable platforms for construction of heterocyclic compounds, such as pyridine, pyrimidine, indolizidine, quinolizidine, and pyrrole derivatives, which are common motifs in alkaloid structures. Little is known about α-enaminones, apparently because they are often not directly accessible from the corresponding diketones. Compared with β-enaminones, the chemical behavior of the α-keto derivatives differs. They can react as enamines (nucleophiles), as well as α,β-unsaturated ketones (electrophiles). Although many strategies are available for utilizing β-enaminones as building blocks, methods for the preparation of heterocycles using α-ketoenamines are limited, and typically require harsh, functional group-intolerant conditions.

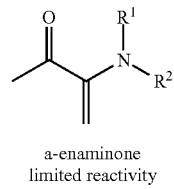

a-enaminone
limited reactivity

-continued

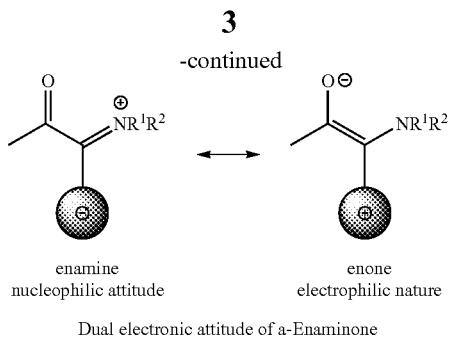

enamine
nucleophilic attitude enone
electrophilic nature

Dual electronic attitude of α-Enaminone

Oxazine, azaspirone, quinolines, quinolinone and quinolinol structures are frequently observed as scaffold segments in various biochemical compounds. These architectures have been identified as building blocks of a numerous alkaloids, as well as other families of diverse, and often remotely related metabolites. Unfortunately, access to a large number of these target molecules, and their structural analogues, is either unknown or hindered by the multistep syntheses. An indepth analysis of the introduced cores suggests that α-enaminone scaffold of Type-1 (Scheme 1) has the potential to serve as an operational, collective key unit for their construction via controlled intramolecular cyclizations.

Scheme 1

Cyclohexyl-based general structure Type-1 was selected to demonstrate the "dual attitude" concept Single precursor
Single methodology
Single-step operation
Regio- and Chemoselective

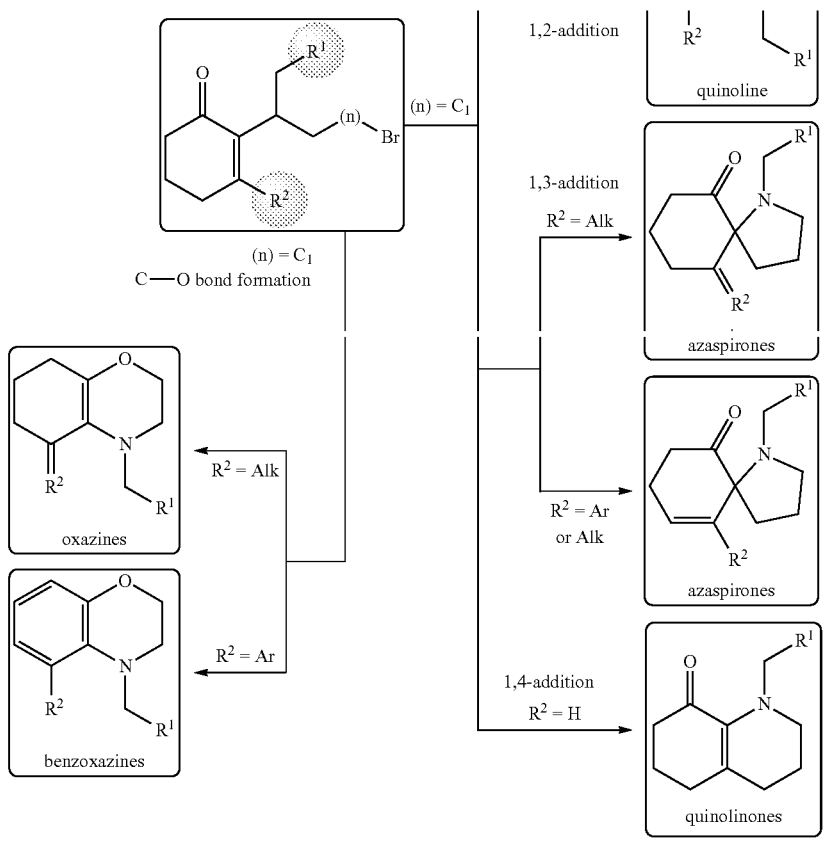

The inventors of the present application have for the first time linked simple and single enaminone core with such a diverse, heterocyclic architectures, and developed a novel streamlined synthetic methodology that allows the rapid and collective composition of multiple targets using a single common precursor. The inventors have found that the reactivity of α,β-enaminones driven by their "dual electronic attitude", harnessing it to provide unexplored, stable α-enaminone synthones, radically different from other known α- or β-counterparts by their chemical behavior, and unlocked unusual functionalities of these building blocks. The general synthesis of several important classes of heterocycles via controlled cyclizations of an easily accessible α-enaminone common key precursors is demonstrated herein.

GENERAL DESCRIPTION

The invention provides a process for the preparation of a heterocyclic compound comprising the step of:

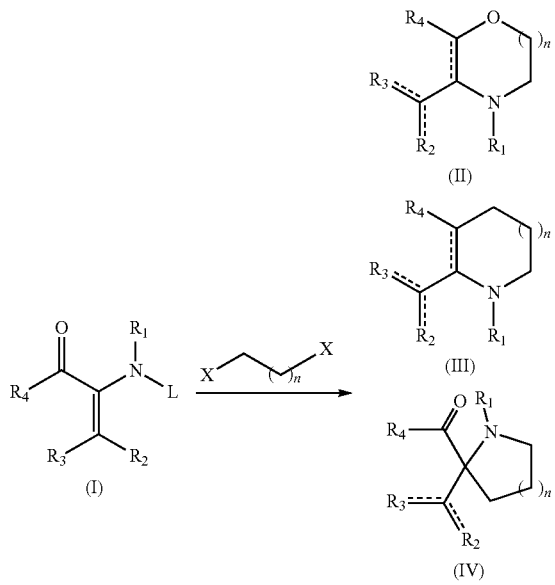

Wherein
X is a halogen;
------ is a single or double bond;
R1-R4 are each independently selected from H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; or
$R_3$ and $R_4$ together with the atoms they are attached to form a 5 to 15 saturated, unsaturated or aromatic ring;
L is a leaving group;
n is an integer between 1 to 10;
And wherein

| When $R_2$ is | And n is | Main Product produces is/are |
|---|---|---|
| H | Greater than 1 | Compound (VI) |
| straight or branched $C_1$-$C_{15}$ alkyl, straight or branched $C_2$-$C_{15}$ alkenyl, straight or branched $C_2$-$C_{15}$ alkynyl, optionally substituted as above | Greater than 1 | Compound (IV) and Compound (V) |
| | 1 | Compound (II) |
| $C_5$-$C_{12}$ aryl, $C_5$-$C_{12}$ heteroaryl; optionally substituted as above | Greater than 1 | Compound (III) and Compound (IV) |
| | 1 | Compound (II) |

In some embodiments, the process of the invention includes the step of:

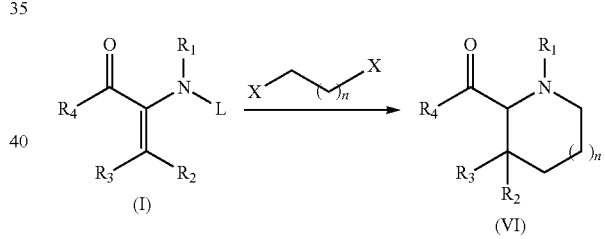

wherein R2 is H and n is greater than 1.
In other embodiments, a process of the invention includes the step of:

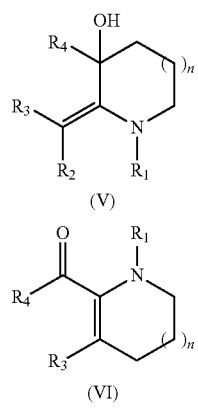

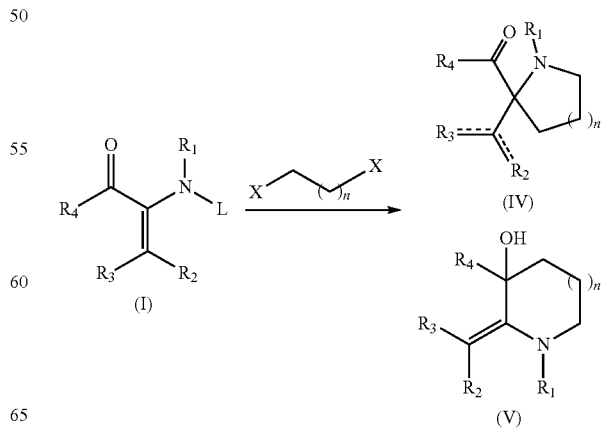

Wherein R2 is straight or branched $C_1$-$C_{15}$ alkyl, straight or branched $C_2$-$C_{15}$ alkenyl, straight or branched $C_2$-$C_{15}$ alkynyl, optionally substituted as defined above and n is greater than 1.

In another embodiment, a process of the invention includes the step of:

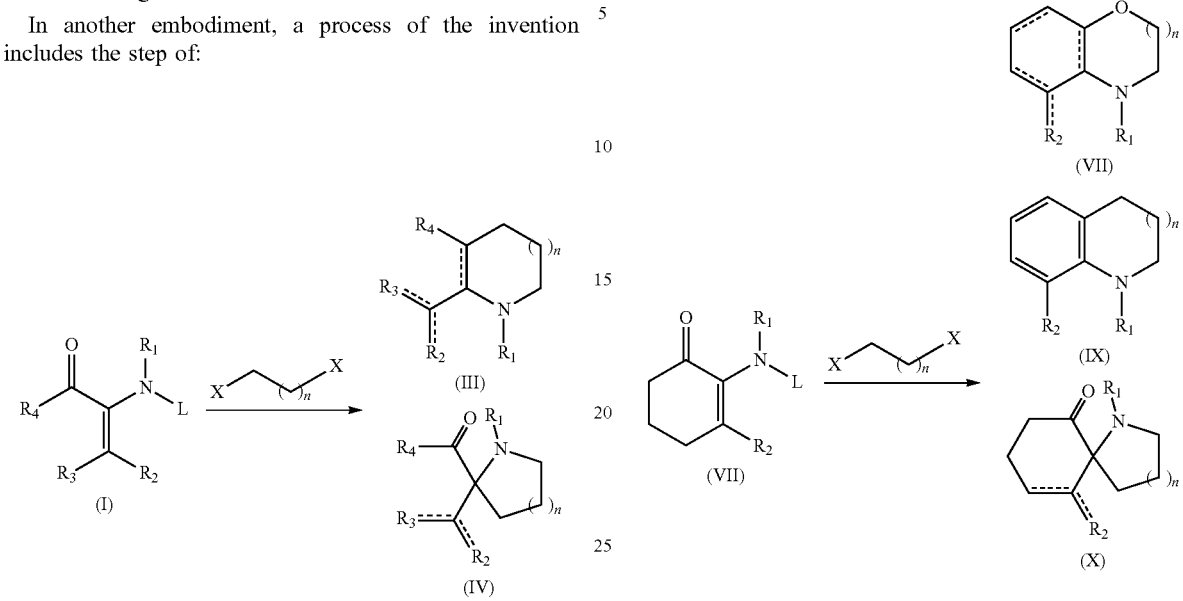

Wherein R2 is $C_5$-$C_{12}$ aryl, $C_5$-$C_{12}$ heteroaryl; optionally substituted as above and n is greater than 1.

In further embodiments, a process of the invention includes the step of:

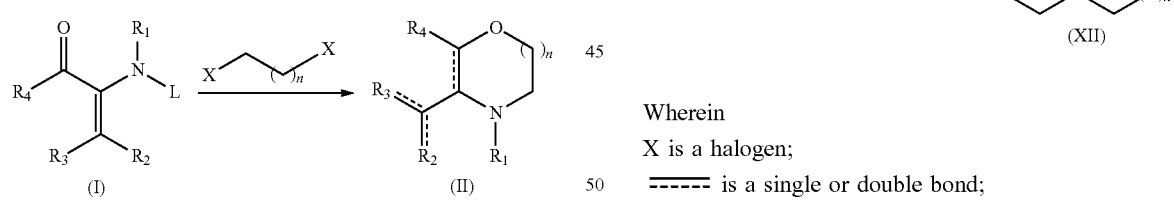

Wherein R2 is straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; and n is 1.

In another embodiment a process of the invention includes the step of:

[Structures VII, IX, X, XI, XII shown]

Wherein

X is a halogen;

------ is a single or double bond;

R1-R4 are each independently selected from H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; or $R_3$ and $R_4$ together with the atoms they are attached to form a 5 to 15 saturated, unsaturated or aromatic ring;

L is a leaving group;

n is an integer between 1 to 10;

And wherein

| When $R_2$ is | And n is | Main Product produces is/are |
|---|---|---|
| H | Greater than 1 | Compound (XII) |
| straight or branched $C_1$-$C_{15}$ alkyl, straight or branched $C_2$-$C_{15}$ alkenyl, straight or branched $C_2$-$C_{15}$ alkynyl, optionally substituted as above | Greater than 1 | Compound (XI) and Compound (X) |
| | 1 | Compound (VIII) |
| $C_5$-$C_{12}$ aryl, $C_5$-$C_{12}$ heteroaryl; optionally substituted as above | Greater than 1 | Compound (IX) and Compound (X) |
| | 1 | Compound (VIII) |

In some embodiments a process of the invention is:

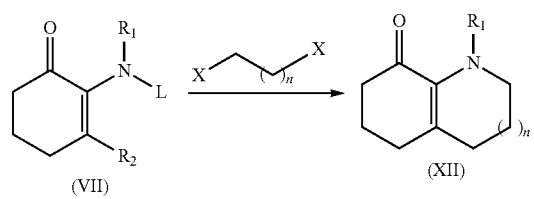

(VII) → (XII)

Wherein $R_2$ is H and n is greater than 1.
In other embodiments, a process of the invention is:

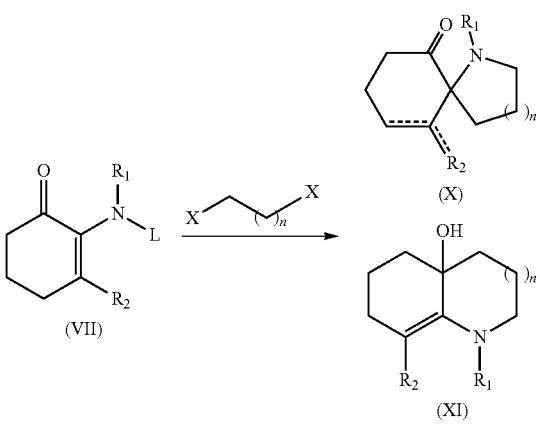

Wherein $R_2$ is straight or branched $C_1$-$C_{15}$ alkyl, straight or branched $C_2$-$C_{15}$ alkenyl, straight or branched $C_2$-$C_{15}$ alkynyl, optionally substituted as defined above and n is greater than 1.

In another one of its embodiments, a process of the invention includes the step of:

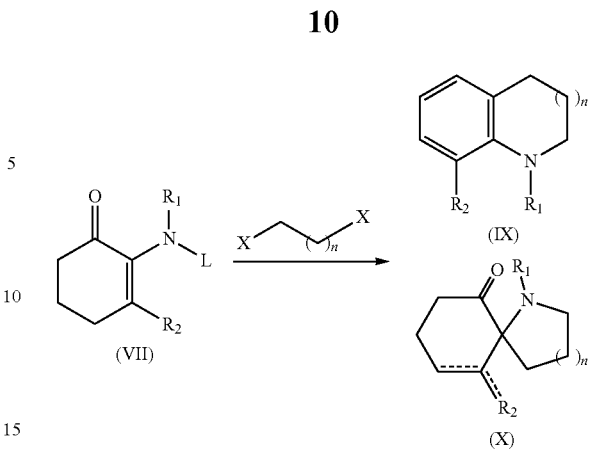

Wherein $R_2$ is $C_5$-$C_{12}$ aryl, $C_5$-$C_{12}$ heteroaryl; optionally substituted as above and n is greater than 1.

In other embodiments a process of the invention includes the step of:

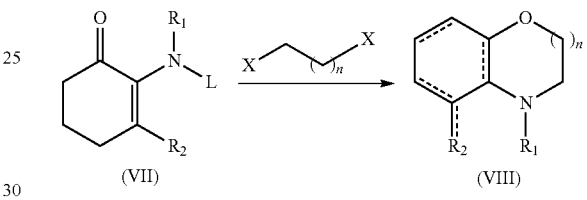

Wherein $R_2$ is straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_2$ heterocycloalkyl; and n is 1.

In some embodiments L is H.

The invention further provides a compound having the general formula (XX):

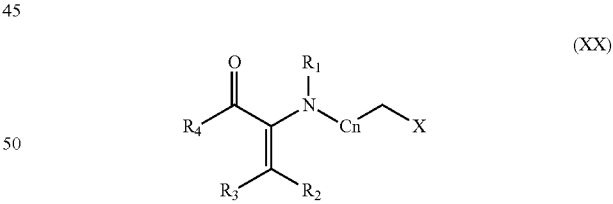

Wherein
X is a halogen;
$R_1$-$R_4$ are each independently selected from H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; provided that at least one of $R_1$-$R_4$ are different than H;

or $R_3$ and $R_4$ together with the atoms they are attached to form a 5 to 15 saturated, unsaturated or aromatic ring;

n is an integer between 1 to 10.

In some embodiments, at least two of $R_1$-$R_4$ are different than H. In other embodiments, at least three of $R_1$-$R_4$ are different than H.

In a further aspect the invention provides a compound having the general formula (XXI):

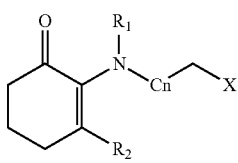

(XXI)

Wherein

X is a halogen;

$R_1$ and $R_2$ is each independently selected from H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl;

n is an integer between 1 to 10.

In some embodiments, at least one of $R_1$-$R_2$ is different than H.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As used herein, the term "acyl," refers to a carbonyl attached to an alkenyl, alkyl, aryl, cycloalkyl, heteroaryl, heterocyclyl, or any other moiety where the atom attached to the carbonyl is carbon. An "acetyl" group refers to a —C(=O)CH$_3$ group. An "alkylcarbonyl" or "alkanoyl" group refers to an alkyl group attached to the parent molecular moiety through a carbonyl group. Examples of such groups include, but are not limited to, methylcarbonyl or ethylcarbonyl. Examples of acyl groups include, but are not limited to, formyl, alkanoyl or aroyl.

As used herein, the term "alkenyl," refers to a straight-chain or branched-chain hydrocarbon group having one or more double bonds and containing from 2 to 20 carbon atoms. A ($C_2$-$C_6$)alkenyl has from 2 to 6 carbon atoms.

As used herein, the term "alkoxy," refers to an alkyl ether group, wherein the term alkyl is as defined below. Examples of suitable alkyl ether groups include, but are not limited to, methoxy, ethoxy, n-propoxy, isopropoxy, n-butoxy, iso-butoxy, sec-butoxy, tert-butoxy, or n-pentoxy.

As used herein, the term "alkyl," refers to a straight-chain or branched-chain alkyl group containing from 1 to 20 carbon atoms. A ($C_1$-$C_{10}$)alkyl has from 1 to 10 carbon atoms and a ($C_1$-$C_6$)alkyl has from 1 to 6 carbon atoms and a ($C_1$-$C_4$)alkyl has from 1 to 4 carbon atoms.

Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or nonyl.

As used herein, the term "alkylene" refers to an alkyl group attached at two positions, i.e. an alkanediyl group. Examples include, but are not limited to, methylene, ethylene, propylene, butylene, pentylene, hexylene, heptylene, octylene, or nonylene. Accordingly, the term "alkylene" may, e.g., refer to a straight-chain or branched-chain alkylene group having from 1 to 6 carbon atoms.

As used herein, the term "alkylamino," refers to an alkyl group attached to the parent molecular moiety through an amino group. Suitable alkylamino groups may be mono- or dialkylated, forming groups including, but not limited to N-methylamino, N-ethylamino, N,N-dimethylamino, N,N-ethyl methylamino, N,N-diethylamino, N-propylamino, and N,N-methylpropylamino.

As used herein, the term "alkynyl," refers to a straight-chain or branched-chain hydrocarbon group having one or more triple bonds and containing from 2 to 20 carbon atoms. A (C2-C6)alkynyl has from 2 to 6 carbon atoms. A (C2-C4) alkynyl has from 2 to 4 carbon atoms. Examples of alkynyl groups include, but are not limited to, ethynyl, propynyl, hydroxypropynyl, butyn-1-yl, butyn-2-yl, pentyn-1-yl, 3-methyl butyn-1-yl, or hexyn-2-yl.

As used herein, the terms "amido" and "carbamoyl," refer to an amino group as described below attached to the parent molecular moiety through a carbonyl group (e.g., —C(=O) NRR'), or vice versa (—N(R)C(=O)R'). "Amido" and "carbamoyl" encompass "C-amido", "N-amido" and "acylamino" as defined herein. R and R' are as defined herein.

As used herein, the term "C-amido," refers to a —C(=O) NRR' group with R and R' as defined herein.

As used herein, the term "amino," refers to —NRR', wherein R and R' are independently selected from the group consisting of hydrogen, alkyl, heteroalkyl, aryl, carbocyclyl, and heterocyclyl. Additionally, R and R' may be combined to form a heterocyclyl.

As used herein, the term "aryl," refers a carbocyclic aromatic system containing one ring, or two or three rings fused together where in the ring atoms are all carbon. The term "aryl" groups includes, but is not limited to groups such as phenyl, naphthyl, or anthracenyl.

As used herein, the term "arylalkoxy" or "aralkoxy," refers to an aryl group attached to the parent molecular moiety through an alkoxy group. Examples of arylalkoxy groups include, but are not limited to, benzyloxy or phenethoxy.

As used herein, the term "arylalkyl" or "aralkyl," refers to an aryl group attached to the parent molecular moiety through an alkyl group.

s used herein, the term "aryloxy," refers to an aryl group attached to the parent molecular moiety through an oxy (—O—).

As used herein, the term "carbamate," refers to an O-carbamyl or N-carbamyl group as defined herein.

As used herein, the term "carbonyl," when alone includes formyl —C(═O)H and in combination is a —C(═O)— group.

As used herein, the term "carboxyl" or "carboxy" refers to —C(═O)OH or the corresponding "carboxylate" anion, such as is in a carboxylic acid salt. An "O-carboxy" group refers to a RC(═O)O— group, where R is as defined herein. A "C-carboxy" group refers to a —C(═O)OR groups where R is as defined herein.

As used herein, the term "cyano" refers to —CN.

As used herein, the term "carbocyclyl" refers to a saturated or partially saturated monocyclic or a fused bicyclic or tricyclic group wherein the ring atoms of the cyclic system are all carbon and wherein each cyclic moiety contains from 3 to 12 carbon atom ring members. "Carbocyclyl" encompasses benzo fused to a carbocyclyl ring system. One group of carbocyclyls have from 5 to 7 carbon atoms. Examples of carbocyclyl groups include, but are not limited to, cyclopropyl, cyclobutyl, cyclopentyl, cyclohexyl, and cycloheptyl, tetrahydronapthyl, indanyl, octahydronaphthyl, 2,3-dihydro-1H-indenyl, or adamantyl.

As used herein, the term "cycloalkyl" refers to a saturated monocyclic, bicyclic or tricyclic group wherein the ring atoms of the cyclic system are all carbon and wherein each cyclic moiety contains from 3 to 12 carbon atom ring members. One group of cycloalkyls has from 5 to 7 carbon atoms. Examples of cycloalkyl groups include, but are not limited to, cyclopropyl, cyclobutyl, cyclopentyl, cyclohexyl, cycloheptyl, or adamantyl.

As used herein, the term "cycloalkenyl" refers to a partially saturated monocyclic, bicyclic or tricyclic group wherein the ring atoms of the cyclic system are all carbon and wherein each cyclic moiety contains from 3 to 12 carbon atom ring members. One group of carboalkenyls have from 5 to 7 carbon atoms. Examples of cycloalkenyl groups include, but are not limited to, cyclobutenyl, cyclopentenyl, or cyclohexenyl.

As used herein, the term "cyclyl" refers to an aryl, heterocyclyl, or carbocyclyl group as defined herein.

As used herein, the term "halo" or "halogen" refers to fluorine, chlorine, bromine, or iodine.

As used herein, the term "haloalkoxy" refers to a haloalkyl group attached to the parent molecular moiety through an oxygen atom. Examples of haloalkoxy groups include, but are not limited to, trifluoromethoxy, 2-fluoroethoxy, or 3-chloropropoxy.

As used herein, the term "haloalkyl" refers to an alkyl group having the meaning as defined above wherein one or more hydrogens are replaced with a halogen. Specifically embraced are monohaloalkyl, dihaloalkyl or polyhaloalkyl groups. A monohaloalkyl group, for one example, may have an iodo, bromo, chloro or fluoro atom within the group. Dihalo or polyhaloalkyl groups may have two or more of the same halo atoms or a combination of different halo groups. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl or dichloropropyl.

As used herein, the term "heteroalkyl" refers to a straight or branched alkyl chain, wherein one, two, or three carbons forming the alkyl chain are each replaced by a heteroatom independently selected from the group consisting of O, N, and S, and wherein the nitrogen and/or sulfur heteroatom(s) (if present) may optionally be oxidized and the nitrogen heteroatom(s) (if present) may optionally be quaternized. The heteroatom(s) O, N and S may, for example, be placed at an interior position of the heteroalkyl group, i.e., the heteroalkyl may be bound to the remainder of the molecule via a carbon atom. Up to two heteroatoms may be consecutive, such as, for example, —CH$_2$—NH—OCH$_3$. Accordingly, a further example for a "heteroalkyl" group is a straight or branched alkyl group, in which two consecutive carbon atoms are replaced by the heteroatoms S and N, respectively, and the sulfur heteroatom is furthermore oxidized, resulting in moieties such as, e.g., —S(═O)$_2$—NH$_2$, —S(═O)$_2$—NH(alkyl) or —S(═O)$_2$—N(alkyl)(alkyl).

As used herein, the term "heteroalkylene" refers to a heteroalkyl group attached at two positions. Examples include, but are not limited to, —CH$_2$OCH$_2$—, —CH$_2$SCH$_2$—, and —CH$_2$NHCH$_2$—, —CH$_2$S—, or —CH$_2$NHCH(CH$_3$)CH$_2$—. Accordingly, the term "heteroalkylene" may, e.g., refer to a straight or branched alkylene group (i.e., a straight or branched alkanediyl group) having from 1 to 6 carbon atoms, wherein 1, 2 (if present) or 3 (if present) of said carbon atoms are each replaced by a heteroatom independently selected from O, N or S. It is to be understood that the presence of hydrogen atoms will depend on the valence of the heteroatom replacing the respective carbon atom. If, for example, the carbon atom in a —CH$_2$— group is replaced by O or S, the resulting group will be —O— or —S—, respectively, while it will be —N(H)— when the carbon atom replaced by N. Likewise, if the central carbon atom in a group —CH$_2$—CH(—CH$_3$)—CH$_2$— is replaced by N, the resulting group will be —CH$_2$— N(—CH$_3$)—CH$_2$—. An example for a "heteroalkylene" group is a straight or branched alkylene group, in which two consecutive carbon atoms are replaced by the heteroatoms S and N, respectively, and the sulfur heteroatom is furthermore oxidized, resulting in moieties such as, e.g., —S(═O)$_2$—N(H)— or —S(═O)$_2$—N(alkyl)-. Accordingly, the groups —S(═O)$_2$—N(H)— and —S(═O)$_2$—N (alkyl)- (e.g., —S(═O)$_2$—N(C$_1$-C$_6$ alkyl)-) are exemplary "heteroalkylene" groups.

As used herein, the term "heteroaryl," refers to a 3 to 7 membered unsaturated monocyclic ring, or a fused monocyclic, bicyclic, or tricyclic ring system in which the rings are aromatic and which at least one ring contains at least one atom selected from the group consisting of O, S, and N. One group of heteroaryls has from 5 to 7 carbon atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocyclyl" or "hetercycle," each refer to a saturated, partially unsaturated, or fully unsaturated monocyclic, bicyclic, or tricyclic heterocyclic group containing at least one heteroatom as a ring member, wherein each said heteroatom may be independently selected from the group consisting of nitrogen, oxygen, and sulfur wherein the nitron or sulfur atoms may be oxidized (e.g., —N═O, —S(═O)—, or —S(═O)$_2$—). Additionally, 1, 2, or 3 of the carbon atoms of the heterocyclyl may be optionally oxidized (e.g., to give an oxo group or ═O). One group of heterocyclyls has from 1 to 4 heteroatoms as ring members. Another group of heterocyclyls has from 1 to 2 heteroatoms as ring members. One group of heterocyclyls has from 3 to 8 ring members in each ring. Yet another group of heterocyclyls has from 3 to 7 ring members in each ring. Again another group of heterocyclyls has from 5 to 6 ring members in each ring. "Heterocyclyl" is intended to encompass a heterocyclyl group fused to a carbocyclyl or benzo ring systems. Examples of heterocyclyl groups include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, or imidazolidinyl. Examples of heteroaryls that are heterocyclyls include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, or furopyridinyl.

As used herein, the term "heterocycloalkyl," refers to a heterocyclyl group that is not fully saturated e.g., one or more of the rings systems of a heterocycloalkyl is not aromatic. Examples of heterocycloalkyls include piperazinyl, morpholinyl, piperidinyl, or pyrrol idinyl.

As used herein, the term "hydroxyl," as used herein, refers to —OH.

As used herein, the term "hydroxyalkyl," as used herein, refers to a hydroxyl group attached to the parent molecular moiety through an alkyl group.

As used herein, the term "nitro," refers to —NO$_2$.

As used herein, the terms "sulfonate" "sulfonic acid" and "sulfonic," refers to the —SO$_3$H group and its anion as the sulfonic acid is used in salt formation.

As used herein, the term "sulfanyl," to —S—.

As used herein, the term "sulfinyl," refers to —S(═O)(R)—, with R as defined herein.

As used herein, the term "sulfonyl," refers to —S(═O)$_2$R, with R as defined herein As used herein, the term "sulfonamide", refers to an N-sulfonamido or S-sulfonamido group as defined herein.

As used herein, the term "N-sulfonamido," refers to a RS(═O)$_2$N(R')— group with R and R' as defined herein. Exemplary, non-limiting N-sulfonamido groups are —NHSO$_2$CH$_3$, —NHSO$_2$CH$_2$CH$_3$, —NHSO$_2$(phenyl), or —NHSO$_2$(isopropyl).

As used herein, the term "S-sulfonamido," refers to a —S(═O)$_2$NRR', group, with R and R' as defined herein.

As used herein, the term "urea," refers to a —N(R)C(═O)N(R) group wherein R and R' are as defined herein.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

As used herein, the term "optically active," refers to the ability of a compound to rotate plane polarized light. In the context of the invention, the term refers to mixtures of enantiomers which are not racemic mixtures; that is to say, not a 50:50 mixture of a (+) enantiomer and the corresponding (−) enantiomer.

DETAILED DESCRIPTION OF EMBODIMENTS

A simple building block of Type-2 was prepared (Table 1; $R^1$=Et; see SI) and selected as the model precursor. α-Enaminone 4 was obtained by reacting 2 with 1,3-dibromopropane in the presence of K$_3$PO$_4$ (1$^{st}$ equivalent of base). Surprisingly, an unexpected direct cyclization was observed. During the preparation of 4, the alkylation of 2 with dibromopropane led to the isolation of stable bicyclic quinolinone system 3 rather than the anticipated α-enaminone. It was assumed that subsequent fast cyclization of 4 yields compound 3 as exclusive single product. Presumably, an equilibrium between 5 and 4 is established due to prevailing enamine-type

TABLE 1

Rapid composition of Quinolinones: 1,4-addition

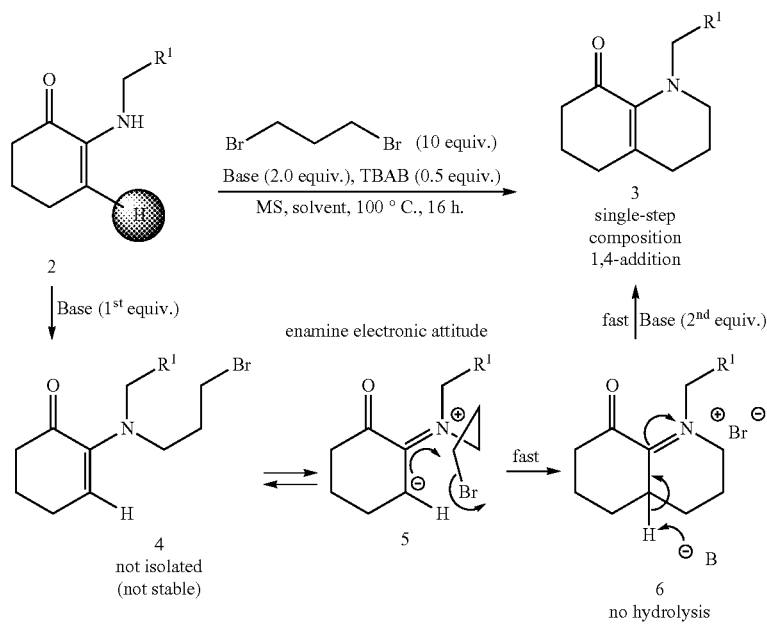

Conditions evaluation for $R^1$ = Et (compound 7)

| # | Base | Solvent | Additive | 3:2 (%)[a] |
|---|------|---------|----------|------------|
| 1 | $K_2CO_3$ | THF | — | 29:44 |
| 2 | $K_2CO_3$ | DMF | — | nr |
| 3 | $K_2CO_3$ | MeCN | — | nr |
| 4 | $K_2CO_3$ | Pyridine | — | 0:93 |
| 5 | $K_2CO_3$ | Toluene | — | 29:65 |
| 6 | $Cs_2CO_3$ | Toluene | — | 26:51 |
| 7 | t-BuOK | Toluene | — | 5:76 |
| 8 | $K_3PO_4$ | Toluene | — | 9:87 |
| 9 | $K_3PO_4$ | Toluene | MS, TBAB 20% | 13:81 |
| 10 | $K_3PO_4$ | Toluene | MS, TBAB 50% | 80:10[b] |
| 11 | $K_3PO_4$ | Toluene | MS, TBAB 100% | 70:15 |
| 12 | $K_2CO_3$ | Toluene | MS, TBAB 50% | 13:41[c] |

Substrate scope[d]

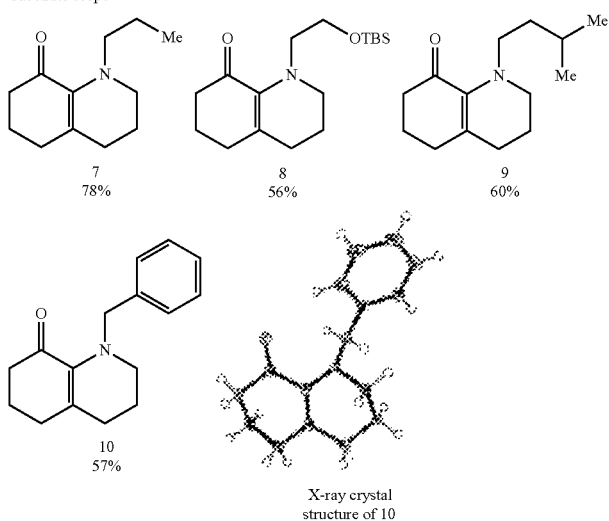

X-ray crystal structure of 10

[a] GC yields: 0.2 mmol scale. [b] All attempts to increase the conversion rate by elevating the temperature or prolonging the reaction time resulted in decomposition of starting materials. [c] The decline in mass balance was due to the degradation of starting precursor during the reaction course. [d] Isolated yields: 0.5 mmol scale.

Subsequent nucleophilic attack leads to favorable 6-membered ring 6. In the presence of a second equivalent of base, the deprotonation of 6 occurs, generating product 3. No hydrolysis of 6 was detected, and only 3 was observed, which suggests that a very fast deprotonation may have occurred. This deprotonation allows the formation of the thermodynamically favorable product while preserving its α,β-unsaturated functionality. An efficient system for the desired transformation involves a combination of 2 with 10 equivalents of 1,3-dibromopropane, 0.5 equivalents of TBAB, and 2 equivalents of $K_3PO_4$ at 100 éC in toluene (entry 10, Table 1). Control experiments were performed and demonstrated that no cyclization occurred in the absence of base. Additional experiments were conducted with various α-enaminone precursors bearing different $R^1$ groups (Table 1) under the optimized cyclization conditions. Exclusive 1,4-selectivity was detected, which led to the generation of quinolinone scaffolds 7-10.[12]

An unexpected cyclization caught our attention when precursor 11 ($R^2 \neq H$) was subjected to 1,2-di bromoethane (Table 2). During the preparation of α-enaminone 13, the rapid cyclization led to the unforeseen isolation of stable oxazine-12 (general structure). Surprisingly, 13 delivers two different outcomes (i.e., 12a-methylene-oxazine or 12b-benzoxazine) depending on the nature of the $R^2$ substituent. The best system for C—O bond formation involves a combination of 11 with 2 equivalents of 1,2-dibromoethane, 0.2 equivalents of TBAB and 2 equivalents of base at 100 éC. Table 2 lists the conditions evaluated for α-enaminone integrated with the aliphatic $R^2$ group (with DIE A as optimal base; entry 6). Then, the same set of variables was applied to the starting material, bearing an aromatic $R^2$ residue. For this setting, $K_2CO_3$ has been determined to be the best base. It was believed that in the presence of base, the deprotonation of 13 is established (two variants are possible depending on the $R^2$ substituent; Scheme 2). The subsequent nucleophilic attack of the oxygen, which was driven by the enone transient attitude, leads further to more favorable 6-membered ring scaffolds that bear a conjugated double bond system (i.e., 12a) or fully aromatized oxazine (i.e., 12b). Representative examples of methylene- and benzoxazines, that were synthesized through C—O bond formation, shown in the Table 2. For this transformation, compounds with a variety of $R^1$— and $R^2$— substituted Type-11 cores were prepared (see SI section) and subjected to the optimized conditions. It is also imperative to mention the exclusive E-selectivity was observed for cyclization products 16-19. The critical stereochemical assignment of the bicyclic targets has been confirmed by NM R analysis (see SI).[13]

As shown in Table 2, the isolated yields of compounds 20-21 were significantly lower than of those of 16-19. The apparent difference between these two groups was attributed to the nature of their $R^2$ residue. As proposed in the Table, an aromatic $R^2$ (in the presence of base) enables formation of a stable resonance form (23) of starting precursor 22, which dramatically slows down the alkylation step towards α-enaminone 24. This result is confirmed by our ability to recover a vast amount of unreacted starting materials. In contrast, the compounds integrated with aliphatic $R^2$ groups did not transform into the resonance form, and most likely undergo the desired alkylations to generate bicyclic products.

TABLE 2

Annulation of α-enaminone via C—O bond formation: Synthesis of methylene- and benzoxazines.

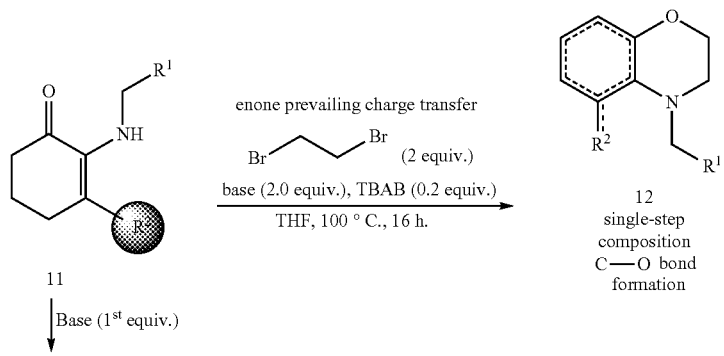

TABLE 2-continued
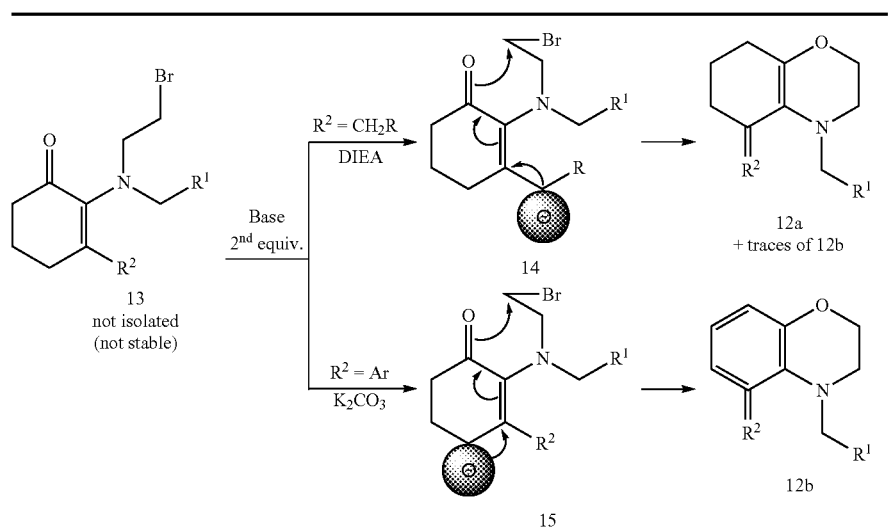
R[1] = Ph, R[2] = Et (compound 17)
| # | Base | Solvent | Yield (%) 12:11[a] |
|---|------|---------|---------------------|
| 1 | $K_2CO_3$ | Acetone | 62:25 |
| 2 | $Na_2CO_3$ | Acetone | 67:5 |
| 3 | $Cs_2CO_3$ | Acetone | 17:51 |
| 4 | $K_3PO_4$ | Acetone | 55:9 |
| 5 | DIEA | Acetone | 74:3 |
| 6 | DIEA | THF | 85:0 |
| 7 | DIEA | Toluene | 76:9 |
| 8 | DIEA | DMF | 13:0 |
| 9 | DIEA | 1,4-Dioxane | 64:18 |
| 10 | DIEA | Pyridine | nr |
| 11 | DIEA | MeCN | 43:8 |
[a]GC yields: 0.2 mmol scale; Isolated yields: 0.5 mmol scale
R[2] = CH$_2$R    E-steroselective termination
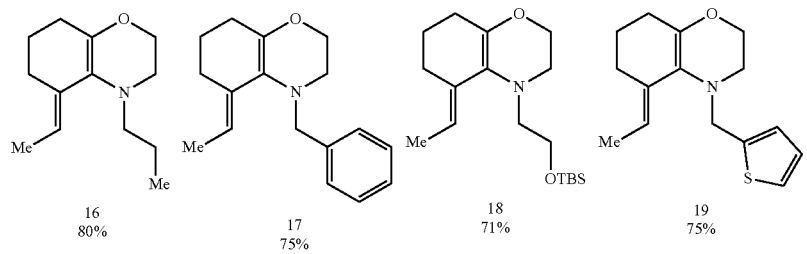
R[2] = Ar
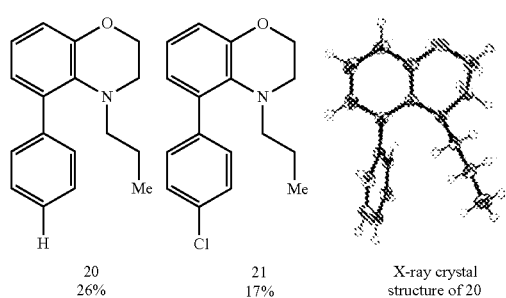
starting material recovered in both cases Effect of resonance contribution on alkylation rate

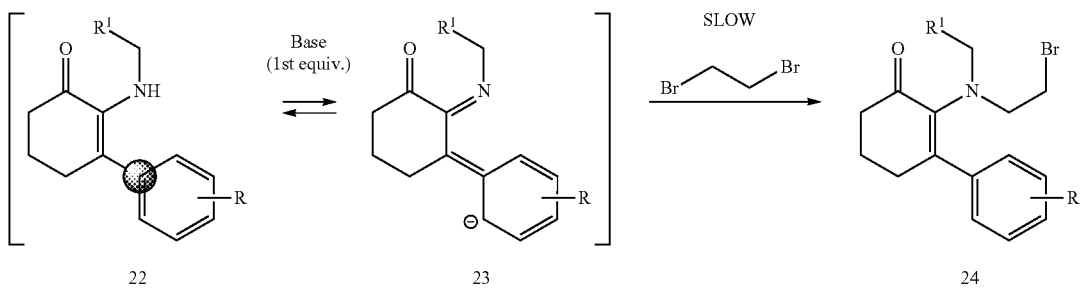

Aromatic R² enables formation of stable resonance form, which dramatically slows down the alkylation step alkylation rate: 20 ( R = H) > 21 (R = Cl)

With suitable access to quinolinones and oxazines in hand, the next experiment was directed to other cyclizations. The reaction scope was extended to the synthesis of more challenging heterocycles using the same precursor (11) as a starting material (Table 3A). An interesting result was observed when 11 ($R^2 \neq H$) was subjected to 1,3-dibromopropane rather than 1,2-dibromo-ethane (as in the previously discussed transformation). In contrast to α-enaminones 4 (Table 1) and 13 (Table 2), the type-27 enaminones were stable (for various $R^1$ and $R^2$). Following the exposure of enaminone 27 to basic conditions (the optimized reaction protocol is provided in Table 4, entry 12), another unexpected and novel cyclization was detected. 1,3-addition was observed, and formation of aza-spirones (Table 3B). The derivatives of 27 were then synthesized and further subjected to the optimized cyclization conditions to generate products 32-39 (Tables 3C and 3D). Interestingly, of the two intermediates (28 and 30; Table 3B), deprotonation primarily occurs at 28 regardless of the nature of $R^2$ group (aliphatic $CH_2R$ or Aromatic). The endo-terminated cyclizations (29) were consistently observed as the dominant products for this transformation. It was postulated that the formation of 31 (minor outcome) is suppressed due to the steric intramolecular hindrance from the R-group, and the alkylbromide chain (30; Table 3B). Enaminone 27a (integrated with the Me group as $R^2$) was prepared and subjected to the optimized cyclization conditions (Table 3E). The ratio of endo and exo products inverts with exo 40b being a major product, which further strengthens our core assumption. Additionally, the effect of the temperature on selectivity of this reaction (1,3-addition) was investigated. Therefore, enaminone 27a (with $R^1$ and $R^2$ being Et groups; Scheme 2) was subjected to cyclization conditions at a lower temperature of 50 éC, utilizing NaOt-Bu as a base.[14] A similar ratio for products 36a and 36b (67:18) was detected. Notwithstanding the lack of selectivity, the successful construction of azaspirones via the 1,3-cyclization of enaminone is remarkable. All pairs of exo- and endo-products were successfully separated, providing access to two conceptually different heterocycles. It should be also mentioned, that the exclusive E-selectivity observed for all exo-terminated products 35b, 36b, 37b, 38b and 39b. The critical stereochemical assignment was confirmed by NMR analysis.[13]

TABLE 3

Synthesis of Azaspirones via 1,3-addition: plausible mechanism, and the substrate scope[a]

A

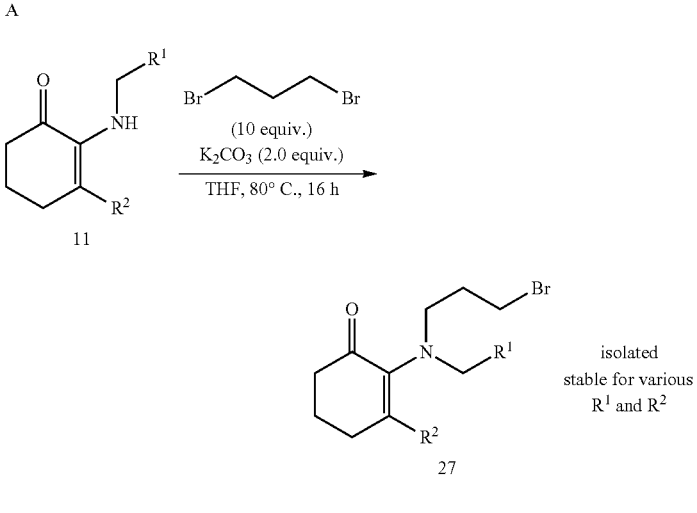

B

TABLE 3-continued
Synthesis of Azaspirones via 1,3-addition: plausible mechanism, and the substrate scope[a]
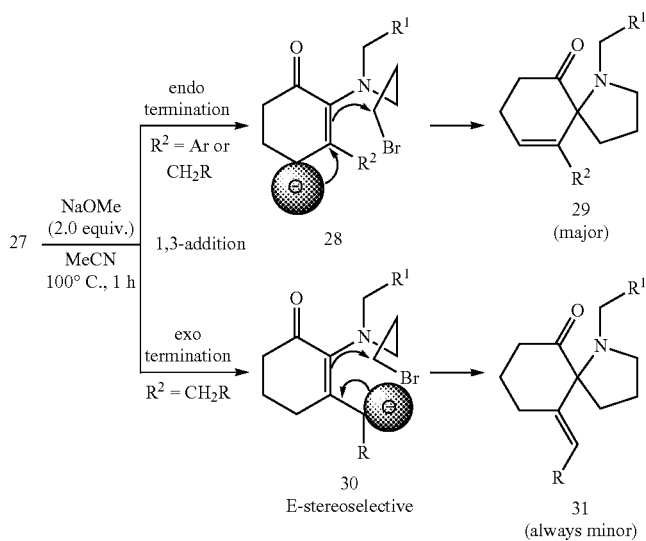
endo
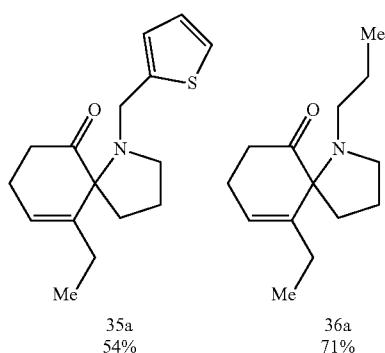 [SMILES: CCC1=CCCC(=O)C12CCCN2Cc1cccs1 ; CCCN1CCCC12C(=O)CCC=C2CC]
35a
54%
36a
71%
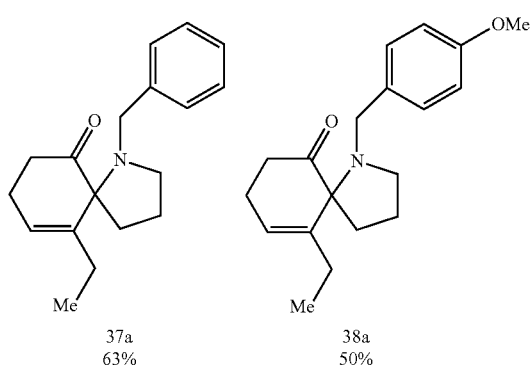 [SMILES: CCC1=CCCC(=O)C12CCCN2Cc1ccccc1 ; CCC1=CCCC(=O)C12CCCN2Cc1ccc(OC)cc1]
37a
63%
38a
50%

TABLE 3-continued
Synthesis of Azaspirones via 1,3-addition: plausible mechanism, and the substrate scope[a]
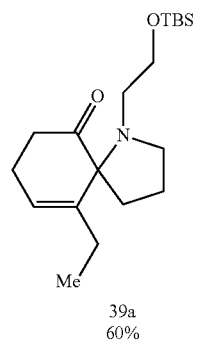 [SMILES: CCC1=CCCC(=O)C12CCCN2CCO[Si](C)(C)C(C)(C)C]
39a
60%
exo
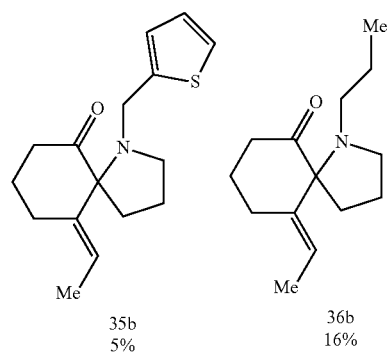 [SMILES: C/C=C1\CCCC(=O)C12CCCN2Cc1cccs1 ; C/C=C1\CCCC(=O)C12CCCN2CCC]
35b        36b
5%         16%
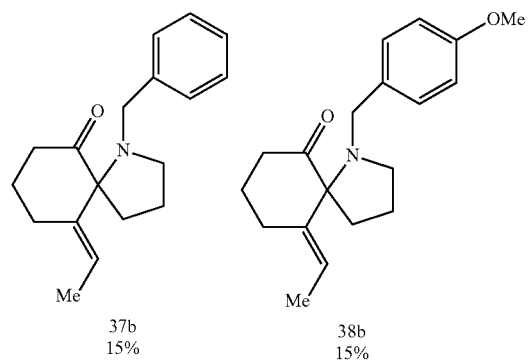 [SMILES: C/C=C1\CCCC(=O)C12CCCN2Cc1ccccc1 ; C/C=C1\CCCC(=O)C12CCCN2Cc1ccc(OC)cc1]
37b        38b
15%        15%
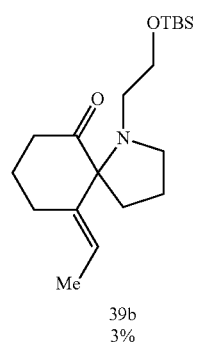 [SMILES: C/C=C1\CCCC(=O)C12CCCN2CCO[Si](C)(C)C(C)(C)C]
39b
3%

TABLE 3-continued
Synthesis of Azaspirones via 1,3-addition: plausible mechanism, and the substrate scope[a]
C 27 → 29
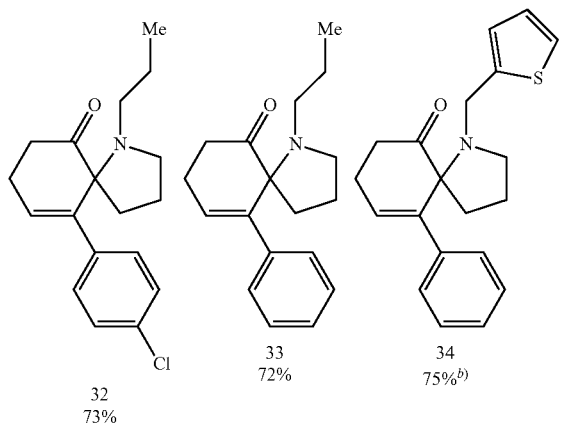
32
73%
33
72%
34
75%[b]
D
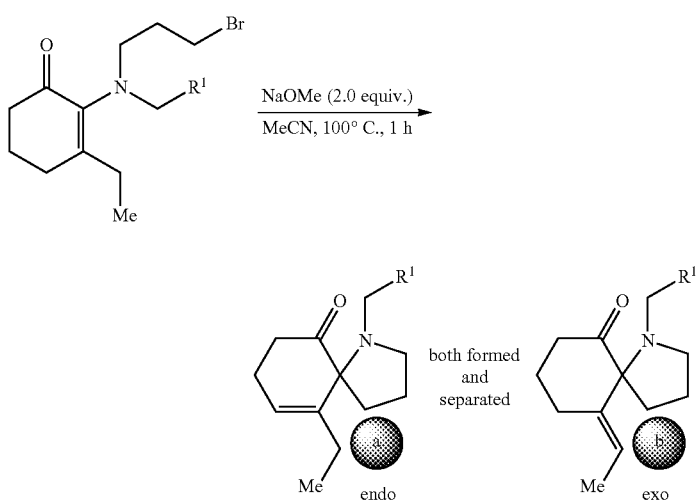
both formed and separated
E Effect of steric hindrance on selectivity: Inversion of the endo and exo products ratio
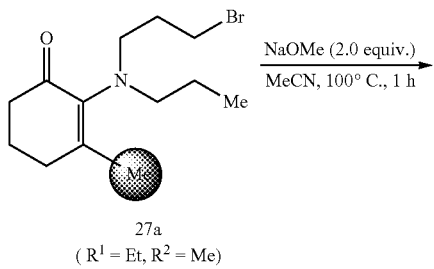 [SMILES: CCCN(CCCBr)C1=C(C)CCCC1=O]
27a
( $R^1$ = Et, $R^2$ = Me)

TABLE 3-continued

Synthesis of Azaspirones via 1,3-addition: plausible mechanism, and the substrate scope[a]

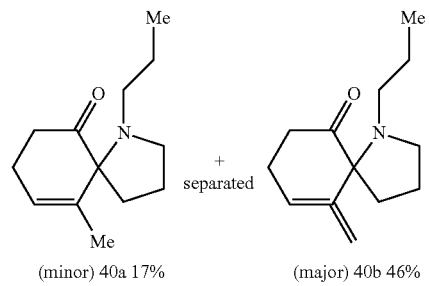

(minor) 40a 17%    (major) 40b 46%

[a]Isolated yields: 0.5 mmol scale. [b]Cs$_2$CO$_3$ was used as base (20 h).

TABLE 4

Conditions evaluation for 1,3-addition
R$^1$ = Ph, R$^2$ = Et (compound 17)

| # | Base | Solvent | Yield (%) 12:11[a] |
|---|---|---|---|
| 1 | K$_2$CO$_3$ | Acetone | 62:25 |
| 2 | Na$_2$CO$_3$ | Acetone | 67:5 |
| 3 | Cs$_2$CO$_3$ | Acetone | 17:51 |
| 4 | K$_3$PO$_4$ | Acetone | 55:9 |
| 5 | DIEA | Acetone | 74:3 |
| 6 | DIEA | THF | 85:0 |
| 7 | DIEA | Toluene | 76:9 |
| 8 | DIEA | DMF | 13:0 |
| 9 | DIEA | 1,4-Dioxane | 64:18 |
| 10 | DIEA | Pyridine | nr |
| 11 | DIEA | MeCN | 43:8 |

[a]GC yields: 0.2 mmol scale

Scheme 2. Effect of temperature on the selectivity.

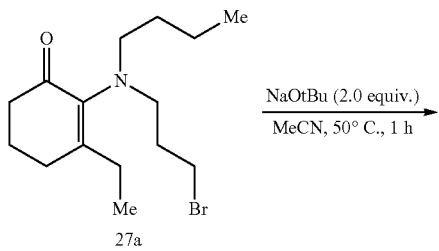

36a 67%    36b 18%    elimination 15%

To complete the picture, the inventors have executed additional cyclizations to investigate the final 1,2-addition of the α-enaminone system. The protocols designed for the radical cyclization of classical enones were followed.[15] The attempts were carried out using the SmI$_2$/HMPA system.[16] Here, type-41 α-enaminones (see SI for preparation) were subjected to radical cyclization conditions to provide bicyclic quinolinols 42 or quinoline 43, however, both were obtained in low yields (Table 5). The two transformations were confirmed to undergo the desired termination, even though reduction and other side products were detected in the reaction mixtures (quinoline was obtained if R$^2$=aromatic). Despite our goal of enhancing the outcome of this transformation by varying the temperature, solvent, concentration, amount of SmI$_2$ or HMPA alternation, and order of reagent addition, our efforts were not successful. Nevertheless, radical reactions of 41 afforded the desired products. To the best of our knowledge, these results represent the first examples of intramolecular cyclizations that incorporate quinolinols and quinolines from a simple enaminone. In these less effective cyclizations, the formation of 42 and 43 required 4 equivalents of the Sm reagent, 10 equivalents of HMPA, and 10 equivalents of tert-butyl alcohol. Regardless of the mentioned drawbacks, the successful construction of the reported heterocycles via this type of transformation is unprecedented and unique.

TABLE 5

Radical 1,2-cyclization: direct access to Quinolines and Quinolinols.

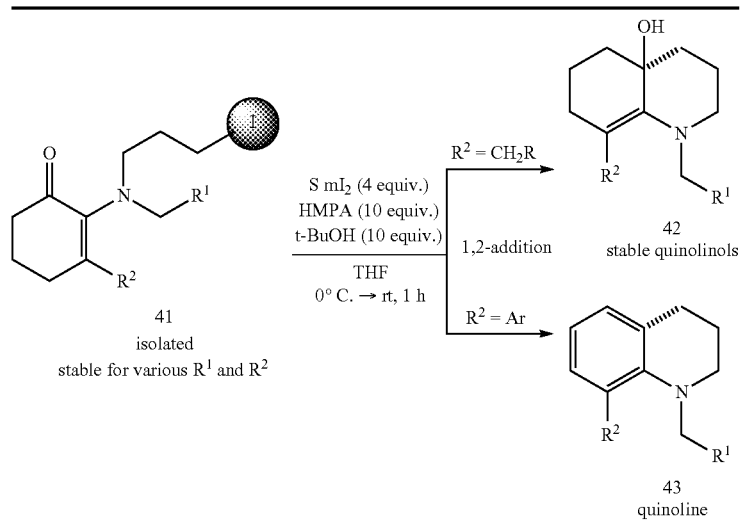

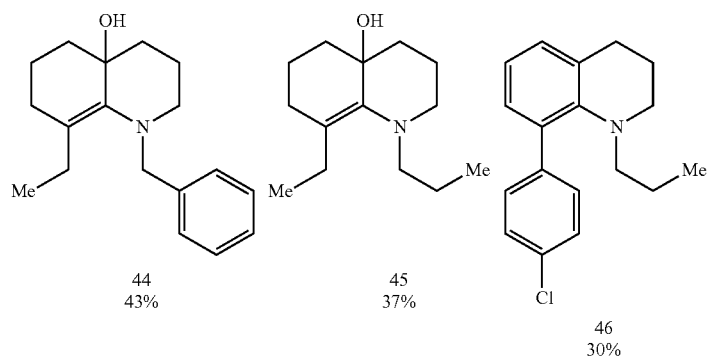

elimination and reduction products isolated in all reactions

The inventors report the unprecedented reactivity of α,β-unsaturated enaminones driven by their "dual electronic attitude", introducing novel, stable α-enaminone synthones and discovered the unusual and novel functionalities of these building blocks. Readily available α-enaminone precursors undergo facile cyclizations under basic conditions to afford a broad spectrum of heterocycles, such as azaspirones, quinolinones, quinolines, quinolinols and oxazines. Accurate design of the starting material allows for specific and selective functionalization reactions across the unsaturated scaffold, enabling the preparation of diverse products.

Experimental Section

General

Unless otherwise noted, all reagents were purchased from commercial suppliers and used without further purification. Solvents used in the reactions were distilled from appropriate drying agents prior to use.

Reactions were monitored by thin-layer chromatography (TLC) on silica gel 60 $F_{254}$ aluminium plates (Merck) and/or gas chromatography-mass spectrometry (GCMS). Visualization of compounds on TLC was accomplished by irradiation with UV light at 254 nm, iodine or vanillin stain. GCMS Analysis was performed with 'Agilent 7820A' gas chromatograph equipped with 'Agilent 5975' quadrupole mass selective detector, using Agilent HP-5MS capillary column (30 m, 0.25 mm, 0.25 μm film).

Column chromatography was performed using silica gel 60 (particle size 0.040-0.063 mm) purchased from Sigma-Aldrich or aluminium oxide 90 active basic (particle size 0.063-0.200 mm) purchased from Merck.

Proton and carbon NM R spectra were recorded on Varian Mercury 300 MHz or Varian Mercury 500 MHz spectrometer in deuterated solvent. Proton chemical shifts are reported in ppm (δ) relative to tetramethylsilane with the solvent resonance employed as the internal standard ($CDCl_3$, δ 7.26 ppm). $^{13}C$ chemical shifts are reported in ppm from tetramethylsilane with the solvent resonance as the internal standard ($CDCl_3$, δ 77.0 ppm). Data are reported as follows: chemical shift, multiplicity (s=singlet, d=doublet, t=triplet, q=quartet, m=multiplet), integration and coupling constants (Hz). High resolution mass spectra were determined on a Thermo Scientific LTQ Orbitrap XL (FTMS).

Infrared spectra (IR) were recorded on a Thermo Fischer Scientific NICOLET iS10 spectrometer.

Unless otherwise noted, the diastereomeric ratios were calculated from GCMS analysis of the crude reaction mixture.

2. General Procedure A: Synthesis of Quinolinones (1,4-Addition)

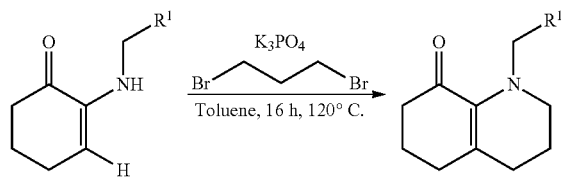

To a flame-dried 15.0 mL reaction tube flushed with nitrogen, fitted with a magnetic stirring bar and rubber septum, were added imminone (1.0 equiv.), $K_3PO_4$ (2.0 equiv.), dibromopropane (10.0 equiv.), TBAB (0.5 equiv.) and molecular sieves (4Å, 500 mg, 1.0 mmol) in dry toluene (0.1 M) at room temperature. The reaction mixture was refluxed at 100 éC for 16 h. The mixture was then concentrated in vacuo, and the crude mixture was purified by flash chromatography to yield the desired product.

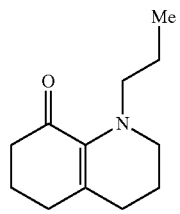 [SMILES: CCCN1CCCC2=C1C(=O)CCC2]

7: 1-Propyl-1,3,4,5,6,7-hexahydroquinolin-8(2H)-one General procedure A was applied. α-Iminone (1) (77 mg, 0.5 mmol) prepared according to General Procedure E, $K_3PO_4$ (212 mg, 1.0 mmol), dibromopropane (1.01 g, 5.0 mmol), TBAB (83 mg, 0.25 mmol) and molecular sieves (4 Å, 250 mg) were mixed in dry toluene (5.0 mL) at room temperature. The reaction mixture was refluxed at 100 éC for 16 h. The mixture was then concentrated in vacuo and the crude product was purified by flash chromatography (Silica gel, 4/96% MeOH/DCM) to yield 7 in 78% yield (75 mg) as yellow liquid. $^1$H NMR (300 MHz, CDCl$_3$): δ 2.93-2.87 (m, 2H), 2.72-2.63 (m, 2H), 2.46-2.35 (m, 2H), 2.27 (t, J=6.2 Hz, 2H), 2.11 (t, J=6.6 Hz, 2H), 1.89 (p, J=6.3 Hz, 2H), 1.71-1.52 (m, 4H), 0.85 (t, J=7.4 Hz, 3H). $^{13}$C NMR (75 MHz, CDCl$_3$): δ 196.20, 141.09, 139.17, 54.61, 47.59, 39.29, 31.10, 29.74, 22.51, 21.96, 18.54, 11.49. IR (neat): 2930, 2868, 2824, 1671, 1603, 1184 cm$^1$. HRMS (m/z) calcd. for C$_{12}$H$_{19}$NONa ([M+Na]+): 216.1359; found: 216.1356.

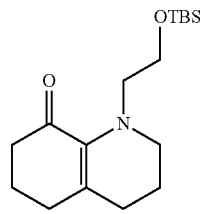 [SMILES: CC(C)(C)[Si](C)(C)OCCN1CCCC2=C1C(=O)CCC2]

8: 1-(2-((tert-Butyldimethylsilyl)oxy)ethyl)-1,3,4,5,6,7-hexahydroquinolin-8(2H)-one General procedure A was applied. α-Iminone (2) (135 mg, 0.5 mmol) prepared according to General Procedure E, $K_3PO_4$ (212 mg, 1.0 mmol), dibromopropane (1.01 g, 5.0 mmol), TBAB (83 mg, 0.25 mmol) and molecular sieves (4 Å, 250 mg) were mixed in dry toluene (5.0 mL) at room temperature. The reaction mixture was refluxed at 100 éC for 16 h. The mixture was then concentrated in vacuo and the crude product was purified by flash chromatography (Silica gel, 5/95% ether/hexane) to yield 8 in 58% yield (90 mg) as yellow liquid. $^1$H NMR (300 MHz, CDCl$_3$): δ 3.82 (t, J=6.7 Hz, 2H), 3.00-2.93 (m, 2H), 2.87 (t, J=6.7 Hz, 2H), 2.44-2.36 (m, 2H), 2.26 (t, J=6.2 Hz, 2H), 2.11 (t, J=6.6 Hz, 2H), 1.89 (p, J=6.3 Hz, 2H), 1.67 (p, J=6.3 Hz, 2H), 0.87 (s, 9H), 0.05 (s, 6H). $^{13}$C NMR (75 MHz, CDCl$_3$): δ 196.23, 140.74, 138.84, 62.87, 54.83, 49.31, 39.21, 31.04, 29.62, 25.94, 22.49, 18.90, −5.33. IR (neat): 2927, 2855, 1673, 1251, 1099, 832, 774 cm$^{-1}$. HRMS (m/z) calcd. for C$_{17}$H$_{31}$NO$_2$Si ([M+Na]$^+$): 332.2016; found: 322.2019.

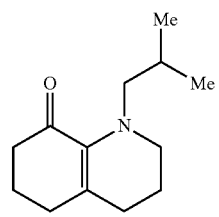 [SMILES: CC(C)CN1CCCC2=C1C(=O)CCC2]

9: 1-Isobutyl-1,3,4,5,6,7-hexahydroquinolin-8(2H)-one General procedure A was applied. α-Iminone (3) (84 mg, 0.5 mmol) prepared according to General Procedure E, $K_3PO_4$ (212 mg, 1.0 mmol), dibromopropane (1.01 g, 5.0 mmol), TBAB (83 mg, 0.25 mmol) and molecular sieves (4Å, 250 mg) were mixes in dry toluene (5 mL) at room temperature. The reaction mixture was refluxed at 100 éC for 16 h. The mixture was then concentrated in vacuo and the crude product was purified by flash chromatography (Silica gel, 20/80% ethyacetate/hexane) to yield 9 in 57% yield (59 mg) as yellow liquid. $^1$H NM R (300 MHz, CDCl$_3$): δ 2.95-2.86 (m, 2H), 2.56 (d, J=7.3 Hz, 2H), 2.40 (t, J=7.4 Hz, 2H), 2.27 (t, J=6.2 Hz, 2H), 2.12 (t, J=6.6 Hz, 2H), 2.02-1.84 (m, 3H), 1.73-161 (m, 2H), 0.93 (d, J=6.7 Hz, 6H). $^{13}$C NMR (75 MHz, CDCl$_3$): δ 196.14, 141.47, 138.70, 59.80, 47.64, 39.54, 31.23, 29.82, 27.69, 22.44, 20.63, 18.31. IR (neat): 2951, 2866, 2822, 1671, 1602, 1435, 1184, 1121, 978 cm$^{-1}$. HRMS (m/z) calcd. for C$_{13}$H$_{21}$NO ([M+Na]$^+$): 230.1515; found: 230.1519.

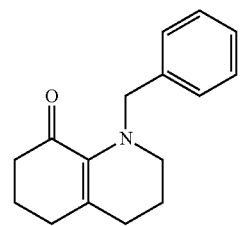 [SMILES: O=C1CCCC2=C1N(Cc1ccccc1)CCC2]

10: 1-Benzyl-1,3,4,5,6,7-hexahydroquinolin-8(2H)-one General procedure A was applied. α-Iminone (4) (101 mg, 0.5 mmol) prepared according to General Procedure E, $K_3PO_4$ (212 mg, 1.0 mmol), dibromopropane (1.01 g, 5.0 mmol), TBAB (83 mg, 0.25 mmol) and molecular sieves (4Å, 250 mg) were mixed in dry toluene (5 mL) at room temperature. The reaction mixture was refluxed at 100 éC for 16 h. The mixture was then concentrated in vacuo and the crude product was purified by flash chromatography (Silica gel, 20/80% ether/hexane) to yield 10 in 54% yield (66 mg) as pale yellow solid (M.p. 86-89 éC). $^1$H NMR (300 MHz, CDCl$_3$): δ 7.48-7.43 (m, 2H), 7.34-7.19 (m, 3H), 3.93 (s, 2H), 2.80-2.76 (m, 2H), 2.50-2.44 (m, 2H), 2.31 (t, J=6.2 Hz, 2H), 2.12 (t, J=6.5 Hz, 2H), 1.95 (p, J=6.3 Hz, 2H), 1.67-1.57 (m, 2H). $^{13}$C NMR (75 MHz, CDCl$_3$): δ 196.13, 140.72, 140.52, 139.79, 129.05, 128.10, 126.88, 55.71, 46.54, 39.44, 31.15, 29.85, 22.51, 17.83. IR (neat): 2943, 2928, 2864, 1661, 1611, 1161, 946, 746, 702 cm$^{-1}$. HRMS (m/z) calcd. for C$_{16}$H$_{19}$NO ([M+H]$^+$): 242.1539; found: 242.1538.

3. General Procedure B: Synthesis of Oxazines (C—O Formation)

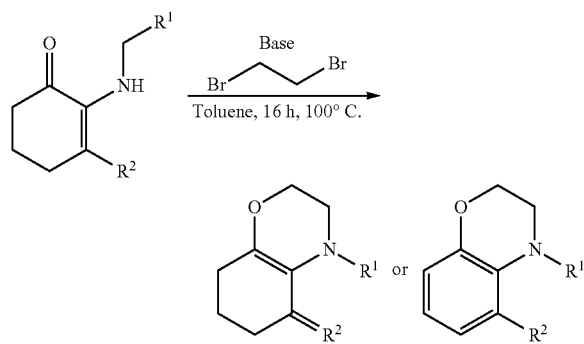

To a flame-dried 15 mL reaction tube, fitted with a magnetic stirring bar and a rubber septum connected to a nitrogen source, □-iminone (1.0 equiv.), base (2.0 equiv.), TBAB (0.2 equiv.), dibromoethane (2.0 equiv.) were mixed in dry THF (0.5M) at room temperature. The reaction mixture was refluxed at 100 éC for 16 h. The mixture was then concentrated in vacuo and the crude mixture was purified by flash chromatography to yield the desired product.

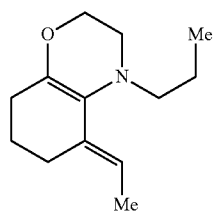 [SMILES: C/C=C1\CCCC2=C1N(CCC)CCO2]

16: 5-Ethylidene-4-propyl-3,4,5,6,7,8-hexahydro-2H-benzo[b][1,4]oxazine General procedure B was applied. α-Iminone (5) (91 mg, 0.5 mmol) prepared according to General Procedure E, Hunig's base (130 mg, 1.0 mmol), TBAB (33 mg, 0.1 mmol) and dibromoethane (188 mg, 1.0 mmol) were mixed in dry THF (1.0 mL) at room temperature. The reaction mixture was refluxed at 100 éC for 16 h. The mixture was then concentrated in vacuo and the crude mixture was purified by flash chromatography (basic alumina, 5/95% ether/hexane) to yield 16 in 80% yield 84 mg) as yellow liquid. $^1$H NMR (300 MHz, CDCl$_3$): δ 5.48 (q, J=7.1 Hz, 1H), 3.97-3.90 (m, 2H), 2.94 (t, J=4.3 Hz, 2H), 2.56-2.47 (m, 2H), 2.22 (q, J=6.6 Hz, 4H), 1.62-1.74 (m, 5H), 1.54 (h, J=7.4 Hz, 2H), 0.88 (t, J=7.4 Hz, 3H). $^{13}$C NMR (75 MHz, CDCl$_3$): δ 140.03, 132.48, 122.04, 112.02, 59.48, 54.99, 45.68, 27.93, 25.28, 22.43, 21.78, 13.21, 11.49. IR (neat): 2958, 2929, 2869, 1624, 1455, 1353, 1143, 700 cm$^{-1}$. HRMS (m/z) calcd. for C$_{13}$H$_{21}$NO ([M+H]$^+$): 208.1696; found: 208.1690.

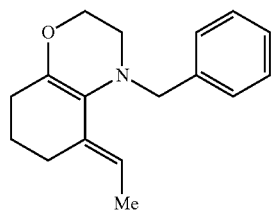 [SMILES: C/C=C1\CCCC2=C1N(Cc1ccccc1)CCO2]

17: 4-Benzyl-5-ethylidene-3,4,5,6,7,8-hexahydro-2H benzo[b][1,4]oxazine General procedure B was applied, α-Iminone (6) (115 mg, 0.5 mmol) prepared according to General Procedure E, Hunig's base (130 mg, 1 mmol), TBAB (33 mg, 0.1 mmol) and di bromoethane (188 mg, 1.0 mmol) were mixed in dry THF (1.0 mL) at room temperature. The reaction mixture was refluxed at 100 éC for 16 h. The mixture was then concentrated in vacuo and the crude product was purified by flash chromatography (basic alumina, 5/95% ether/hexane) to yield 17 in 75% yield (95 mg) as yellow liquid. $^1$H NMR (300 MHz, CDCl3): δ 7.43 (d, J=7.6 Hz, 2H), 7.35 (t, J=7.4 Hz, 2H), 7.31-7.23 (m, 1H), 5.70 (q, J=7.2 Hz, 1H), 3.99-3.95 (m, 2H), 3.93 (s, 2H), 2.90 (t, J=4.4 Hz, 2H), 2.30 (q, J=6.7 Hz, 4H), 1.77 (q, J=6.4 Hz, 2H), 1.69 (d, J=6.9 Hz, 3H). $^{13}$C NMR (75 MHz, CDCl3): δ 140.97, 139.40, 132.24, 128.44, 127.81, 126.86, 121.35, 112.00, 59.44, 56.40, 45.75, 27.98, 25.35, 22.49, 13.30. IR (neat): 2957, 2928, 2864, 1642, 1624, 1194, 1146, 731, 696 cm$^{-1}$. HRMS (m/z) calcd. for C$_{17}$H$_{21}$NO ([M+H]$^+$): 256.1696; found: 256.1693.

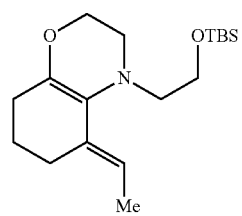 [SMILES: C/C=C1\CCCC2=C1N(CCO[Si](C)(C)C(C)(C)C)CCO2]

18: 5-Ethylidene-4-propyl-3,4,5,6,7,8-hexahydro-2H-benzo[b][1,4]oxazine General procedure B was applied. α-Iminone (7) (149 mg, 0.5 mmol) prepared according to General Procedure E, Hunig's base (130 mg, 1.0 mmol), TBAB (33 mg, 0.1 mmol) and dibromoethane (188 mg, 1.0 mmol) were mixed in dry THF (1.0 mL) at room temperature. The reaction mixture was refluxed at 100 éC for 16 h. The mixture was then concentrated in vacuo and the crude mixture was purified by flash chromatography (basic alumina, 5/95% ether/hexane) to yield 18 in 71% yield 95 mg) as yellow liquid. $^1$H NM R (300 MHz, CDCl3): δ 5.54 (q, J=7.2 Hz, 1H), 3.96 (t, J=4.4 Hz, 2H), 3.76 (t, J=6.3 Hz, 2H), 3.03 (t, J=4.4 Hz, 2H), 2.73 (t, J=6.4 Hz, 2H), 2.23 (q, J=6.2 Hz, 4H), 1.63-1.75 (m, 5H), 0.90 (s, 9H), 0.07 (s, 6H). $^{13}$C NMR (75 MHz, CDCl3): δ 140.12, 132.35, 121.74, 112.35, 62.63, 59.67, 55.15, 47.12, 27.93, 25.94, 25.27, 22.39, 18.33, 13.21, −5.35. IR (neat): 2957, 2930, 2859, 1456, 1249, v1098, 837, 770 cm$^{-1}$. HRMS (m/z) calcd. for C$_{18}$H$_{33}$NO$_2$Si ([M+H]$^+$): 324.2353; found: 324.2354.

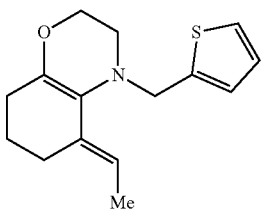 [SMILES: C/C=C1\CCCC2=C1N(Cc1cccs1)CCO2]

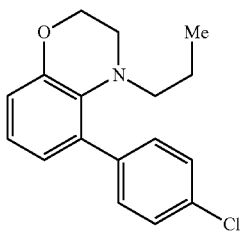

19: 5-Ethylidene-4-(thiophen-2-yl methyl)-3,4,5,6,7,8-hexahydro-2H-benzo[b][1,4]oxazine General procedure B was applied. α-Iminone (8) (118 mg, 0.5 mmol) prepared according to General Procedure E, Hunig's base (130 mg, 1.0 mmol), TBAB (33 mg, 0.1 mmol) and dibromoethane (188 mg, 1.0 mmol) were mixed in dry THF (1.0 mL) at room temperature. The reaction mixture was refluxed at 100 éC for 16 h. The mixture was then concentrated in vacuo and the crude product was purified by flash chromatography (basic alumina, 5/95% ether/hexane) to yield 19 in 71% yield (93 mg) as yellow liquid. $^1$H NM R (300 MHz, CDCl$_3$): δ 7.27-7.22 (m, 1H), 6.99-6.91 (m, 2H), 5.77 (q, J=7.1 Hz, 1H), 4.01 (s, 2H), 3.95 (t, J=4.4 Hz, 2H), 3.00-2.92 (m, 2H), 2.36-2.23 (m, 4H), 1.82-1.67 (m, 5H). $^{13}$C NMR (75 MHz, CDCl$_3$): δ 143.73, 141.06, 132.01, 126.52, 124.84, 124.58, 120.87, 112.27, 59.56, 51.79, 45.68, 27.89, 25.30, 22.40, 13.30. IR (neat): 2955, 2928, 2858, 1455, 1246, 1094, 830, 771 cm$^1$. HRMS (m/z) calcd. for C$_{15}$H$_{19}$NOS ([M+H]$^+$): 262.1260; found: 262.1251.

21: 5-(4-Chlorophenyl)-4-propyl-3,4,5,6,7,8-hexahydro-2H-benzo[b][1,4]oxazine General procedure B was applied. α-Iminone (10) (132 mg, 0.5 mmol) prepared according to General Procedure E, K$_2$CO$_3$ (138 mg, 1.0 mmol), TBAB (33 mg, 0.1 mmol) and dibromoethane (188 mg, 1.0 mmol) were mixed in dry THF (1.0 mL) at room temperature. The reaction mixture was refluxed at 100 éC for 16 h. The mixture was then concentrated in vacuo and the crude product was purified by flash chromatography (Silica gel, 2/98% Ether/hexane) to yield 21 in 17% yield (49 mg) as yellow liquid. $^1$H NMR (300 MHz, CDCl$_3$): δ 7.50-7.45 (m, 2H), 7.38-7.33 (m, 2H), 6.96-6.83 (m, 2H), 6.74 (dd, J=7.2, 1.9 Hz, 1H), 4.10 (t, J=4.5 Hz, 2H), 3.14 (t, J=4.5 Hz, 2H), 2.50-2.42 (m, 2H), 1.23-1.10 (m, 2H), 0.49 (t, J=7.4 Hz, 3H). $^{13}$C NMR (75 MHz, CDCl$_3$): δ 139.42, 132.50, 130.40, 128.27, 123.36, 122.13, 116.69, 60.21, 57.71, 45.40, 20.69, 11.14. IR (neat): 2964, 2930, 2860, 1580, 1461, 1433, 1240, 1134, 1006, 871, 763, 702 cm$^1$. HRMS (m/z) calcd. for C$_{17}$H$_{18}$ClNO ([M+H]$^+$): 288.1150; found: 288.1152.

4. General Procedure C: Synthesis of Azaspiro-Decanones (1,3 Addition)

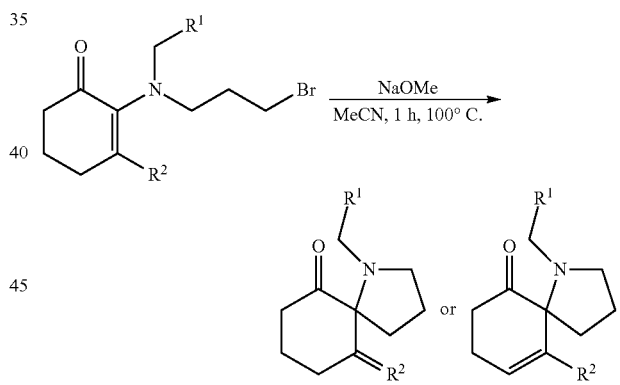

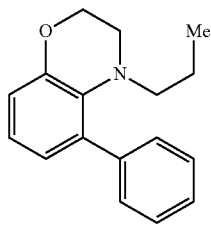 [SMILES: CCCN1CCOc2cccc(-c3ccccc3)c21]

20: 5-Phenyl-4-propyl-3,4,5,6,7,8-hexahydro-2H-benzo[b][1,4]oxazine General procedure B was applied. α-Iminone (9) (115 mg, 0.5 mmol) prepared according to General Procedure E, K$_2$CO$_3$ (138 mg, 1.0 mmol), TBAB (33 mg, 0.1 mmol) and dibromoethane (188 mg, 1.0 mmol) were mixed in dry THF (1.0 mL) at room temperature. The reaction mixture was refluxed at 100 éC for 16 h. The mixture was then concentrated in vacuo and the crude product was purified by flash chromatography (Silica gel, 2/98% ether/hexane) to yield 20 in 26% yield (32 mg) as yellow liquid. $^1$H NMR (300 MHz, CDCl$_3$): δ 7.57-7.52 (m, 2H), 7.41 (dd, J=8.2, 6.6 Hz, 2H), 7.36-7.31 (m, 1H), 6.98-6.86 (m, 2H), 6.82 (dd, J=7.1, 2.0 Hz, 1H), 4.13 (t, J=4.4 Hz, 2H), 3.17 (t, J=4.5 Hz, 2H), 2.54-2.46 (m, 2H), 1.26-1.07 (m, 1H), 0.47 (t, J=7.4 Hz, 3H). $^{13}$C NMR (75 MHz, CDCl$_3$): δ 147.71, 141.07, 136.01, 134.23, 129.09, 128.13, 126.69, 123.59, 121.90, 116.37, 60.33, 57.75, 45.65, 20.70, 11.09. IR (neat): 2964, 2860, 1580, 1461, 1433, 1240, 1006, 871, 775, 702 cm$^{-1}$. HRMS (m/z) calcd. for C$_{17}$H$_{19}$NO ([M+H]$^+$): 276.1357; found: 276.1360.

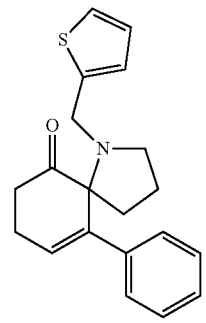 [SMILES: O=C1CCC=C(c2ccccc2)C12CCCN2Cc1cccs1]

To a flame-dried 15 mL reaction tube flushed with nitrogen, fitted with a magnetic stirring bar and rubber septum, were added α-enaminone (1.0 equiv., 0.5 mmol) and NaOMe (2.0 equiv., 1 mmol) in dry MeCN (1M) at o room temperature. The reaction mixture was refluxed at 100 éC for 1 h. The mixture was then concentrated in vacuo and the crude product was purified by flash chromatography to yield the desired product.

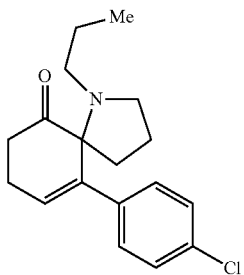 [SMILES: CCCN1CCCC12C(=O)CCC=C2c1ccc(Cl)cc1]

32: 10-(4-Chlorophenyl)-1-propyl-1-azaspiro[4.5]dec-9-en-6-one General procedure C was applied. α-Enaminone (1) (192 mg, 0.5 mmol) prepared according to General Procedure F and NaOMe (54 mg, 1.0 mmol) were mixed in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 32 in 73% yield (111 mg) as pale yellow oil. $^1$H NM R (300 MHz, CDCl$_3$): δ 7.52 (dd, J=6.6, 3.0 Hz, 2H), 7.27 (dd, J=4.9, 1.9 Hz, 3H), 6.13 (t, J=4.2 Hz, 1H), 3.12-3.26 (m, 1H), 2.79 (q, J=8.2 Hz, 1H), 2.56-2.57 (m, 2H), 2.56-2.36 (m, 4H), 1.88-1.77 (m, 3H), 1.69-1.39 (m, 2H), 0.84 (t, J=7.4 Hz, 3H). $^{13}$C NMR (75 MHz, CDCl$_3$): δ 213.43, 143.13, 140.98, 130.28, 129.26, 127.38, 126.86, 73.08, 51.17, 50.33, 39.51, 34.37, 24.38, 22.62, 22.50, 12.08. IR (neat): 2958, 2931, 2871, 2846, 1704, 1486, 1174, 1089, 1015, 822 cm$^{-1}$. HRMS (m/z) calcd. for C$_{18}$H$_{22}$ClNO ([M+H]$^+$): 304.1463; found: 304.1467.

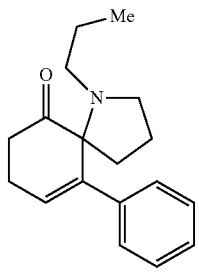 [SMILES: CCCN1CCCC12C(=O)CCC=C2c1ccccc1]

33: 10-Phenyl-1-propyl-1-azaspiro[4.5]dec-9-en-6-one General procedure C was applied. α-Enaminone (2) (175 mg, 0.5 mmol) prepared o according to General Procedure F and NaOMe (54 mg, 1.0 mmol) were mixed in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 33 in 72% yield (97 mg) as pale yellow oil. $^1$H NM R (300 MHz, CDCl$_3$): δ 7.48 (d, J=8.2 Hz, 2H), 7.23 (d, J=8.1 Hz, 2H), 6.12 (t, J=4.2 Hz, 1H), 3.18 (td, J=8.1, 2.7 Hz, 1H), 2.78 (q, J=7.4 Hz, 1H), 2.67-2.35 (m, 6H), 1.90-1.69 (m, 3H), 1.66-1.49 (m, 2H), 1.33-1.47 (m, 1H), 0.83 (t, J=7.4 Hz, 3H). $^{13}$C NMR (75 MHz, CDCl$_3$): δ 213.06, 142.08, 139.32, 132.80, 130.66, 130.55, 127.51, 72.95, 51.10, 50.32, 39.45, 34.43, 24.31, 22.59, 22.48, 12.09. IR (neat): 2957, 2930, 2846, 1704, 1442, 1174, 1075, 759, 698 cm$^{-1}$. HRMS (m/z) calcd. for C$_{18}$H$_{23}$NO ([M+H]$^+$): 270.18524; found: 270.18506.

34: 10-Phenyl-1-(thiophen-2-yl methyl)-1-azaspiro[4.5] dec-9-en-6-one General procedure C was applied. α-Enaminone (3) (202 mg, 0.5 mmol) prepared according to General Procedure F, Cs$_2$CO$_3$ (326 mg, 1.0 mmol) were mixed in dry MeCN (0.5 mL) at room temperature. The reaction mixture was refluxed at 100 éC for 20 h. The mixture was then concentrated in vacuo and the crude product was purified by flash chromatography (Silica gel, 5/95% ether/hexane) to yield 34 in 75% yield (122 mg) as yellow oil. $^1$H NMR (300 MHz, CDCl$_3$): δ 7.62-7.54 (m, 2H), 7.40-7.28 (m, 3H), 7.16 (d, J=5.1, 1.3 Hz, 1H), 6.93-6.86 (m, 1H), 6.81 (d, J=3.4 Hz, 1H), 6.20 (t, J=4.3 Hz, 1H), 4.05-3.86 (m, 2H), 3.10-2.99 (m, 1H), 2.89 (q, J=8.0 Hz, 1H), 2.80-2.68 (m, 1H), 2.60-2.46 (m, 3H), 2.14-2.01 (m, 1H), 2.01-1.78 (m, 2H), 1.77-1.56 (m, 1H). $^{13}$C NMR (75 MHz, CDCl$_3$): δ 212.87, 144.18, 143.11, 140.60, 130.78, 129.36, 127.60, 127.06, 126.11, 125.16, 124.55, 73.17, 50.69, 48.05, 39.06, 35.21, 24.51, 22.46. IR (neat): 2958, 2845, 1704, 1444, 1169, 758, cm$^{-1}$. HRMS (m/z) calcd. for C$_{20}$H$_{21}$NOS ([M+Na]$^+$): 346.1236; found: 346.1236.

35a (endo) and 35b (exo): General procedure C was applied. α-Enaminone (4) (178 mg, 0.5 mmol) prepared according to General Procedure F and NaOMe (54 mg, 1.0 mmol), were mixes in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 54% of 35a and 5% of 35b (65 mg and 7 mg respectively).

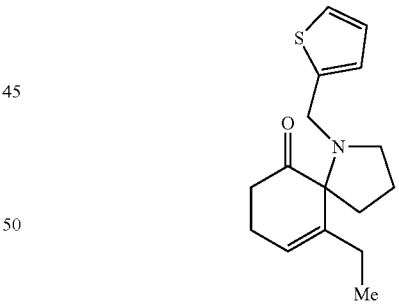

35a: 10-Ethyl-1-(thiophen-2-yl methyl)-1-azaspiro[4.5] dec-9-en-6-one pale yellow solid (M.p. 49-51 éC). $^1$H NM R (300 MHz, CDCl$_3$): δ 7.17 (d, J=5.0, 1.3 Hz, 1H), 6.92-6.84 (m, 2H), 5.88-5.79 (m, 1H), 3.96 (d, J=14.1 Hz, 1H), 3.72 (d, J=14.0 Hz, 1H), 3.17-3.07 (m, 1H), 2.92 (q, J=7.8 Hz, 1H), 2.72-2.58 (m, 1H), 2.44-2.30 (m, 4H), 2.24-2.11 (m, 1H), 2.06-1.94 (m, 1H), 1.90-1.78 (m, 3H), 1.12 (t, J=7.4 Hz, 3H). $^{13}$C NMR (75 MHz, CDCl$_3$): δ 213.58, 145.58, 143.87, 126.25, 124.13, 123.73, 74.04, 50.67, 47.90, 38.69, 35.37, 24.88, 22.64, 22.06, 13.25. IR (neat): 2957, 2924, 2848, 1703, 1177, 722 cm$^{-1}$. HRMS (m/z) calcd. for C$_{16}$H$_{21}$NOS ([M+Na]$^+$): 298.1236; found: 298.1237.

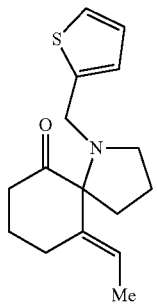 [SMILES: C/C=C1\CCCC(=O)C12CCCN2Cc1cccs1]

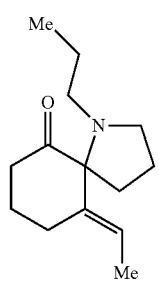

35b: 10-Ethylidene-1-(thiophen-2-yl methyl)-1-azaspiro[4.5]decan-6-one pale yellow solid (M.p. 53-55 éC). $^1$H NMR (300 MHz, CDCl$_3$): δ 7.19 (dd, J=4.8, 1.6 Hz, 1H), 6.93 (d, J=5.2 Hz, 2H), 6.07 (q, J=7.0 Hz, 1H), 4.14 (d, J=14.5 Hz, 1H), 3.72 (d, J=14.5 Hz, 1H), 3.22-3.10 (m, 1H), 2.95-2.84 (m, 1H), 2.79-2.68 (m, 1H), 2.54-2.47 (m, 2H), 2.27-2.10 (m, 2H), 1.97-1.71 (m, 3H), 1.70-1.56 (m, 5H). $^{13}$C NMR (75 MHz, CDCl$_3$): δ 213.77, 145.85, 139.23, 126.30, 124.15, 123.88, 118.49, 79.54, 50.86, 48.59, 39.93, 38.08, 25.91, 22.90, 21.66, 13.27. IR (neat): 2926, 2841, 1702, 1454, 1134, 851, 696 cm$^{-1}$. HRMS (m/z) calcd. for C$_{16}$H$_{21}$NOS ([M+Na]$^+$): 298.1236; found: 298.1236.

36a (endo) and 36b (exo): General procedure C was applied. α-Enaminone (5) (151 mg, 0.5 mmol) prepared according to General Procedure F and NaOMe (54 mg, 1.0 mmol) were mixed in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 71% of 36a and 16% of 36b (78 mg and 18 mg respectively) as pale yellow oils.

36b: 10-Ethylidene-1-propyl-1-azaspiro[4.5]decan-6-one 1H NMR (300 MHz, CDCl$_3$): δ 5.81-5.70 (m, 1H), 3.25-3.17 (m, 1H), 2.93-2.83 (m, 1H), 2.75-2.55 (m, 21H), 2.47-2.38 (m, 2H), 2.33-2.25 (m, 1H), 2.18-2.03 (m, 2H), 1.89-1.82 (m, 1H), 1.76-1.70 (m, 3H), 1.64 (d, J=6.9 Hz, 3H), 1.57-1.39 (m, 3H), 0.86 (t, J=7.4 Hz, 3H). $^{13}$C NMR (75 MHz, CDCl$_3$): δ 214.43, 139.65, 117.77, 51.71, 51.05, 40.11, 38.07, 29.69, 25.76, 22.87, 22.69, 21.61, 13.21, Me 11.97. IR (neat): 2956, 2928, 2668, 1707, 1456, 1197, 1153, 1096 cm$^{-1}$. HRMS (m/z) calcd. for C$_{14}$H$_{23}$NO ([M+H]$^+$): 222.1852; found: 222.1855.

37a (endo) and 37b (exo): General procedure C was applied. α-Enaminone (6) (175 mg, 0.5 mmol) prepared according to General Procedure F and NaOMe (54 mg, 1.0 mmol) were mixed in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 63% of 37a and 15% of 37b (85 mg and 20 mg respectively).

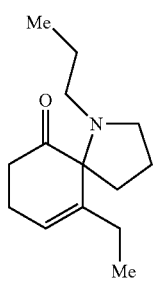 [SMILES: CCCN1CCCC12C(=O)CCC=C2CC]

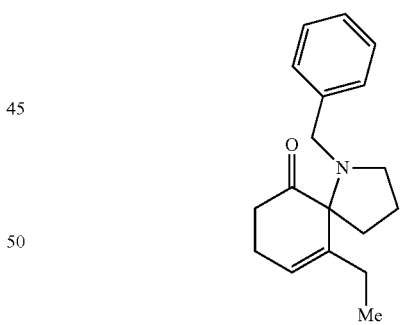

36a: 10-Ethyl-1-propyl-1-azaspiro[4.5]dec-9-en-6-one 1H NMR (300 MHz, CDCl$_3$): δ 5.81-5.72 (m, 1H), 3.20-3.08 (m, 1H), 2.84-2.73 (m, 1H), 2.60-2.46 (m, 1H), 2.45-1.91 (m, 7H), 1.90-1.69 (m, 4H), 1.54-1.19 (m, 2H), 1.03 (t, J=7.5 Hz, 3H), 0.81 (t, J=7.4 Hz, 3H). $^{13}$C NMR (75 MHz, CDCl$_3$): δ 214.52, 144.22, 123.10, 73.64, 50.66, 50.38, 39.27, 34.74, 24.35, 22.71, 22.58, 21.91, 13.18, 11.85. IR (neat): 2958, 2931, 2872, 2847, 1712, 1458, 1180, 1085 cm$^{-1}$. HRMS (m/z) calcd. for C$_{14}$H$_{23}$NO ([M+Na]$^+$): 244.1672; found: 244.1679.

37a: 1-Benzyl-10-ethyl-1-azaspiro[4.5]dec-9-en-6-one pale yellow solid (M.p. 52-55 éC). $^1$H NM R (300 MHz, CDCl$_3$): δ 7.34-7.16 (m, 5H), 5.90-5.82 (m, 1H), 3.76-3.51 (m, 2H), 3.04-2.93 (m, 1H), 2.85 (h, J=6.5 Hz, 1H), 2.73-2.57 (m, 1H), 2.49-2.28 (m, 4H), 2.25-2.14 (m, 1H), 2.05-1.76 (m, 4H), 1.11 (t, J=7.5 Hz, 3H). $^{13}$C NMR (75 MHz, CDCl$_3$): δ 213.99, 143.86, 140.54, 128.14, 128.02, 126.48, 123.77, 73.88, 52.80, 50.51, 39.03, 35.02, 24.68, 22.77, 22.09, Me 13.28. IR (neat): 2961, 2847, 1709, 1494, 1452, 1153, 733, 697 cm$^1$. HRMS (m/z) calcd. for C$_{18}$H$_{23}$NO ([M+H]$^+$): 270.1852; found: 270.1857.

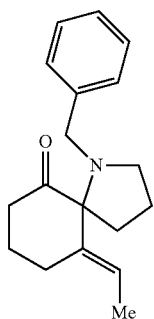 [SMILES: C/C=C1\CCCC(=O)C12CCCN2Cc1ccccc1]

37b: 1-Benzyl-10-ethylidene-1-azaspiro[4.5]decan-6-one pale yellow solid (M.p. 57-58 éC). $^1$H NMR (300 MHz, CDCl$_3$): δ 7.38 (d, J=7.0 Hz, 2H), 7.32 (t, J=7.5 Hz, 2H), 7.26-7.17 (m, 1H), 5.97 (q, J=7.0 Hz, 1H), 3.88 (d, J=14.4 Hz, 1H), 3.65 (d, J=14.6 Hz, 1H), 3.11-3.02 (m, 1H), 2.90-2.79 (m, 1H), 2.77-2.67 (m, 1H), 2.57-2.48 (m, 2H), 2.30-2.13 (m, 2H), 1.97-1.68 (m, 4H), 1.67-1.59 (m, 4H). $^{13}$C NMR (75 MHz, CDCl$_3$): δ 214.07, 140.89, 139.55, 128.14, 127.98, 126.33, 118.28, 79.69, 53.15, 50.72, 39.99, 37.69, 25.94, 22.93, 21.67, 13.28. IR (neat): 2926, 2849, 1703, 1492, 1453, 1209, 1152, 1136, 735, 697 cm$^{-1}$. HRMS (m/z) calcd. for C$_{18}$H$_{23}$NO ([M+Na]$^+$): 292.1672; found: 292.1676.

38a (endo) and 38b (exo): General procedure C was applied. α-Enaminone (7) (209 mg, 0.5 mmol) prepared according to General Procedure F and NaOMe (54 mg, 1.0 mmol) were mixed in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 60% of 38a and 3% of 38b (101 mg and 5 mg respectively) as pale yellow oils.

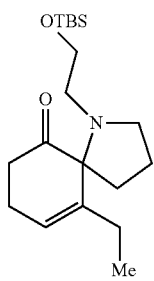 [SMILES: CCC1=CCCC(=O)C12CCCN2CCO[Si](C)(C)C(C)(C)C]

38a: 1-(2-((tert-Butyldimethylsilyl)oxy)ethyl)-10-ethyl-1-azaspiro[4.5]dec-9-en-6-one $^1$H NMR (300 MHz, CDCl$_3$): δ 5.78-5.72 (m, 1H), 3.65-3.51 (m, 2H), 3.22-3.13 (m, 1H), 2.99-2.88 (m, 1H), 2.70-2.47 (m, 3H), 2.42-2.11 (m, 4H), 2.05-1.91 (m, 1H), 1.90-1.64 (m, 4H), 1.03 (t, J=7.4 Hz, 3H), 0.87 (s, 9H), 0.02 (s, 6H). $^{13}$C NMR (75 MHz, CDCl$_3$): δ 214.05, 144.07, 123.18, 74.22, 62.67, 51.63, 51.48, 38.80, 34.77, 25.96, 24.68, 22.98, 21.89, 18.39, 12.92, −5.34. IR (neat): 2956, 2928, 2845, 1714, 1253, 1103, 832, 774 cm$^{-1}$. HRMS (m/z) calcd. for C$_{19}$H$_{35}$NO$_2$Si ([M+H]$^+$): 360.2329; found: 360.2329.

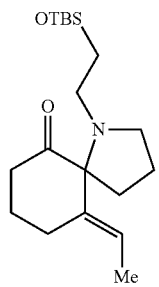 [SMILES: C/C=C1\CCCC(=O)C12CCCN2CCO[Si](C)(C)C(C)(C)C]

38b: 1-(2-((tert-Butyldimethylsilyl)oxy)ethyl)-10-ethyl-idene-1-azaspiro[4.5]decan-6-one $^1$H NMR (300 MHz, CDCl$_3$): δ 5.81 (q, J=6.4 Hz, 1H), 3.77-3.65 (m, 2H), 3.26-3.18 (m, 1H), 3.00-2.78 (m, 2H), 2.76-2.65 (m, 1H), 2.58-2.47 (m, 1H), 2.45-2.38 (m, 2H), 2.20-2.01 (m, 2H), 1.94-1.66 (m, 3H), 1.68-1.45 (m, 5H), 0.89 (s, 9H), 0.05 (s, 6H). $^{13}$C NMR (75 MHz, CDCl$_3$): δ 214.01, 139.45, 118.18, 80.14, 62.78, 52.35, 51.90, 39.98, 37.75, 25.99, 25.82, 22.94, 21.83, 18.42, 13.22, −5.27, −5.31. IR (neat): 2954, 2928, 2856, 1709, 1254, 1104, 834, 775 cm$^{-1}$. HRMS (m/z) calcd. for C$_{19}$H$_{35}$NO$_2$Si ([M+H]$^+$): 360.2329; found: 360.2327.

40a (exo) and 40b (endo): General procedure C was applied. α-Enaminone (8) (144 mg, 0.5 mmol) prepared according to General Procedure F and NaOMe (54 mg, 1.0 mmol) were mixed in dry MeCN (0.5 mL) at room temperature. The reaction mixture was refluxed at 100 éC for 1 h. The mixture was then concentrated in vacuo and the crude product was purified by flash chromatography (Silica gel, 5/95% ether/hexane) to yield 17% of 40a and 46% of 40b (18 mg and 48 mg respectively) as pale yellow oils.

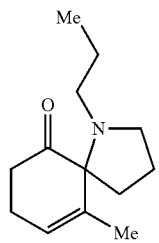 [SMILES: CCCN1CCCC12C(=O)CCC=C2C]

40a: 10-Methyl-1-propyl-1-azaspiro[4.5]dec-9-en-6-one 1H NMR (300 MHz, CDCl$_3$): δ 5.82-5.71 (m, 1H), 3.21-3.09 (m, 1H), 2.88-2.78 (m, 1H), 2.61-2.50 (m, 1H), 2.48-2.37 (m, 1H), 2.38-2.21 (m, 4H), 1.99-1.72 (m, 4H), 1.71 (s, 3H), 1.55-1.28 (m, 2H), 0.84 (t, J=7.4 Hz, 3H). $^{13}$C NMR (75 MHz, CDCl$_3$): δ 214.27, 138.85, 125.69, 73.34, 50.55, 50.36, 39.34, 34.43, 24.41, 22.66, 22.59, Me 17.71, 11.90. IR (neat): 2957, 2930, 2848, 1711, 1448, 1184, 1083, 807 cm$^{-1}$. HRMS (m/z) calcd. for C$_{13}$H$_{21}$NO ([M+H]$^+$): 208.1696; found: 208.1697.

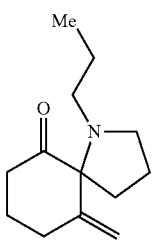

40b: 10-Methylene-1-propyl-1-azaspiro[4.5]decan-6-one
1H NMR (300 MHz, CDCl$_3$): δ 5.19-5.13 (m, 1H), 4.89-4.84 (m, 1H), 3.32-3.22 (m, 1H), 3.00-2.89 (m, 1H), 2.72-2.62 (m, 1H), 2.55 (dt, J=14.0, 4.3 Hz, 1H), 2.48-2.29 (m, 4H), 2.17-2.03 (m, 1H), 1.95-1.72 (m, 4H), 1.64-1.50 (m, 2H), 1.46-1.36 (m, 1H), 0.86 (t, J=7.4 Hz, 3H). $^{13}$C NMR (75 MHz, CDCl$_3$): δ 213.51, 150.10, 109.41, 79.72, 51.78, 51.22, 40.46, 38.75, 33.61, 23.56, 22.90, 21.70, 11.92. IR (neat): 2955, 2934, 2870, 2843, 1708, 1457, 1100, 1082, 905 cm$^{-1}$. HRMS (m/z) calcd. for C$_{13}$H$_{21}$NO ([M+H]$^+$): 208.1696; found: 208.1696.

5. General procedure D: Synthesis of Quinolines and Quinolinols (1,2-addition)

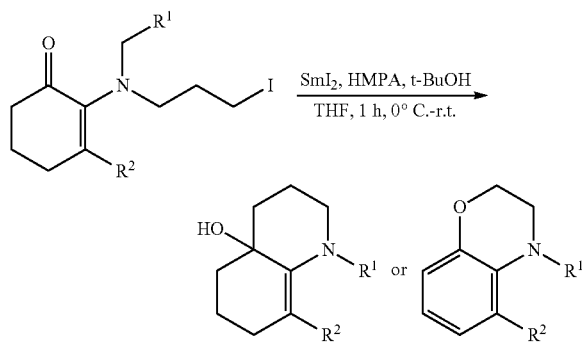

In a flame-dried 100 mL reaction flask flushed with nitrogen, fitted with a magnetic stirring bar and rubber septum a solution of SmI$_2$ in THF (0.1 M, 4.0 equiv.) was added dropwise (1 mL/min) to a solution of α-enaminone (1.0 equiv, 0.5 mmol), HMPA (10.0 equiv., 5.0 mmol) and t-BuOH (10.0 equiv., 5.0 mmol) in dry THF (0.05 M) at 0 éC. The reaction mixture was then stirred under inert atmosphere for 1 h at room temperature and quenched with aqueous saturated NH$_4$Cl. The mixture was extracted with EtOAc, dried over anhydrous Na$_2$SO$_4$, filtered and concentrated in vacuo. The crude mixture was purified by flash chromatography to yield the desired product.

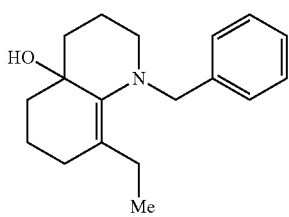 [SMILES: CCC1=C2N(Cc3ccccc3)CCCC2(O)CCC1]

44: 1-Benzyl-8-ethyl-1,3,4,5,6,7-hexahydroquinolin-4a(2H)-ol General procedure D was applied. A solution of SmI$_2$ in THF (20.0 mL, 0.1 M, 2.0 mmol) was added dropwise to a solution of α-enaminone (9) prepared according to General Procedure G, (199 mg, 0.5 mmol), HMPA (895 mg, 5.0 mmol), and t-BuOH (370 mg, 5.0 mmol) in dry THF (10.0 mL) at 0 éC. The reaction mixture was stirred under inert atmosphere for 1 h at room temperature and quenched with aqueous saturated NH$_4$Cl. The mixture was then dried over anhydrous Na$_2$SO$_4$, filtered and concentrated in vacuo. The crude product was purified by flash chromatography (Silica gel, 10/90% EtOAc/hexane) to yield 44 in 43% yield (58 mg) as mixture of 2 diastereomers as yellow liquid. $^1$H NMR (300 MHz, CDCl$_3$): δ 7.42-7.29 (m, 4H), 7.28-7.21 (m, 1H), 4.39 (d, J=14.5 Hz, 1H), 3.83 (d, J=14.3 Hz, 1H), 2.79-2.90 (m, 1H), 2.60 (t, J=12.8, 2.9 Hz, 1H), 2.28 (q, J=7.5 Hz, 2H), 2.17-2.02 (m, 2H), 2.01-1.79 (m, 2H), 1.79-1.71 (m, 1H), 1.59-1.70 (m, 2H), 1.56-1.38 (m, 2H), 1.29-1.14 (m, 1H), 0.99 (t, J=7.6 Hz, 3H). $^{13}$C NMR (75 MHz, CDCl$_3$): δ 142.41, 140.98, 130.13, 128.28, 128.08, 126.70, 69.37, 60.26, 48.13, 39.37, 39.33, 29.28, 24.84, 18.39, 18.07, 12.79. IR (neat): 2930, 2872, 1710, 1459, 942, 734, 697 cm$^1$. HRMS (m/z) calcd. for C$_{18}$H$_{25}$NONa ([M+Na]$^+$): 294.1828; found: 294.1824.

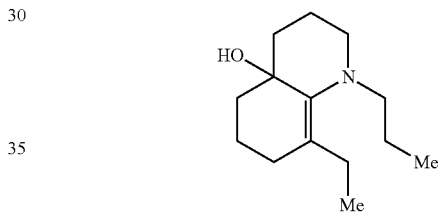

45: 8-Ethyl-1-propyl-1,3,4,5,6,7-hexahydroquinolin-4a(2H)-ol: General procedure D was applied. A solution of SmI$_2$ in THF (20 mL, 0.1 HO M, 2.0 mmol) was added dropwise to a solution of α-enaminone (10) prepared according to General Procedure G, (175 mg, 0.5 mmol), HMPA (895 mg, 5.0 mmol), and t-BuOH (370 mg, 5.0 mmol) in dry THF (10.0 mL) at 0 éC. The reaction mixture was stirred under inert atmosphere for 1 h at room temperature and quenched with aqueous saturated NH$_4$Cl. The mixture was then dried over anhydrous Na$_2$SO$_4$, filtered and concentrated in vacuo. The crude product was purified by flash chromatography (Basic alumina, 5/95% EtOAc/hexane) to yield 45 in 37% yield (41 mg) as mixture of 2 diastereomers as yellow liquid. $^1$H NMR (300 MHz, CDCl$_3$): Mixture of diastereomers: δ 3.09-2.92 (m, 2H), 2.70-2.58 (m, 2H), 2.16-2.06 (m, 3H), 2.04-1.95 (m, 2H), 1.86-1.71 (m, 2H), 1.61-1.53 (m, 2H), 1.52-1.38 (m, 4H), 1.34-1.24 (m, 2H), 0.95 (t, J=7.6 Hz, 3H), 0.87 (t, J=7.4 Hz, 3H). $^{13}$C NMR (75 MHz, CDCl$_3$): Major diastereomer: δ 142.78, 127.72, 69.31, 58.40, 49.22, 39.66, 38.90, 29.50, 25.13, 22.97, 19.59, 18.68, 12.97, 11.63. Minor diastereomer, characteristic signals: δ 79.90, 57.91, 53.66, 42.41, 34.71, 34.05, 23.57, 20.99, 19.44, 18.98, 12.12, 6.71. IR (neat): 3486, 2956, 2925, 2870, 1709, 1670, 1457, 1376, 1088 cm$^{-1}$. HRMS (m/z) calcd. for C$_{14}$H$_{25}$NO ([M+H]$^+$): 224.2009; found: 224.2014.

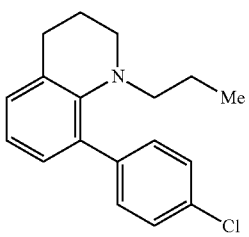 [SMILES: CCCN1CCCc2cccc(-c3ccc(Cl)cc3)c21]

46: 8-(4-Chlorophenyl)-1-propyl-1,2,3,4-tetrahydroquinoline: General procedure D was applied. A solution of SmI$_2$ in THF (20.0 mL, 0.1 M, 2.0 mmol) was added dropwise to a solution of α-enaminone (11) prepared according to General Procedure G, (216 mg, 0.5 mmol), HMPA (895 mg, 5.0 mmol), and t-BuOH (370 mg, 5.0 mmol) in dry THF (10.0 mL) at 0 éC. The reaction mixture was stirred under inert atmosphere for 1 h at room temperature and quenched with aqueous saturated NH$_4$Cl. The mixture was then dried over anhydrous Na$_2$SO$_4$, filtered and concentrated in vacuo. The crude product was purified by flash chromatography (Silica gel, 1/99% EtOAc/hexane) to yield 46 in 30% yield (48 mg) as yellow oil. $^1$H NMR (300 MHz, CDCl$_3$): δ 7.42-7.32 (m, 2H), 7.25 (d, J=8.4 Hz, 2H), 7.15-7.01 (m, 1H), 6.67-6.53 (m, 1H), 6.47 (d, J=7.5, 1.2 Hz, 1H), 3.39-3.17 (m, 4H), 2.57 (t, J=6.3 Hz, 2H), 1.84 (p, J=6.5 Hz, 1H), 1.67 (h, J=7.4 Hz, 2H), 0.97 (t, J=7.4 Hz, 3H). $^{13}$C NMR (75 MHz, CDCl$_3$): δ 145.98, 145.52, 140.93, 132.44, 130.51, 128.02, 126.58, 119.47, 116.92, 109.89, 53.71, 49.41, 26.64, 22.19, 19.54, 11.60, 1.04. IR (neat): 2951, 2925, 2870, 1714, 1582, 1484, 1459, 1199, 1085, 1017, 831, 774, 719 cm$^{-1}$. HRMS (m/z) calcd. for C$_{18}$H$_{20}$ClN ([M+H]$^+$): 286.1357; found: 286.1365.

6. General Procedure E: Preparation of α-Iminones

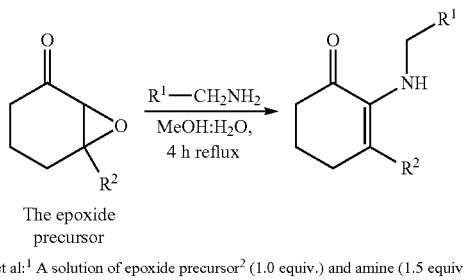

The epoxide precursor

Napier et al:[1] A solution of epoxide precursor[2] (1.0 equiv.) and amine (1.5 equiv.) in 3:1 mixture of methanol:water was refluxed for 4 h. After cooling, the solvent was removed and the residue was diluted with saturated brine solution, extracted with EtOAc, dried (Na$_2$SO$_4$), filtered and concentrated in vacuo. The crude mixture was purified by flash chromatography to yield the desired product.

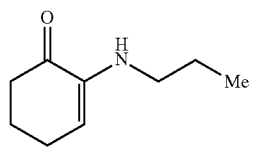 [SMILES: CCCNC1=CCCCC1=O]

α-Iminone 1: 2-(propylamino)cyclohex-2-en-1-one General procedure E was applied. The corresponding epoxide precursor 7-oxabicyclo[4.1.0]heptan-2-one (1.0 g, 9.0 mmol) and propylamine (800 mg, 13.5 mmol) were mixed in 9.0 mL of methanol, and 3.0 mL of water. The mixture was then refluxed for 4 h. After cooling, the solvent was removed and the residue was diluted with saturated brine solution, extracted with EtOAc, dried (Na$_2$SO$_4$), filtered and concentrated in vacuo. The crude product was purified by flash chromatography (Silica gel, 10/90% EtOAc/hexane) to yield the desired product in 63% yield (865 mg) as yellow liquid. $^1$H NMR (300 MHz, CDCl$_3$): δ 5.32 (t, J=4.7 Hz, 1H), 4.15-3.90 (m, 1H), 2.71 (t, J=7.0 Hz, 2H), 2.42-2.32 (m, 2H), 2.28 (q, J=5.6 Hz, 2H), 1.50 (h, J=7.3 Hz, 2H), 0.87 (t, J=7.4 Hz, 3H). $^{13}$C NMR (75 MHz, CDCl3): δ 195.71, 140.61, 110.56, 44.93, 37.87, 24.47, 23.48, 22.08, 11.69. IR (neat): 3399, 2958, 2931, 2872, 1671, 1626, 1488, 1167, 867 cm$^{-1}$. HRMS (m/z) calcd. for C$_9$H$_{15}$NO ([M+H]$^+$): 154.1226; found: 154.1228.

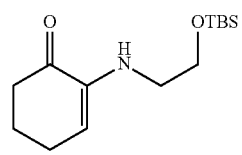 [SMILES: CC(C)(C)[Si](C)(C)OCCNC1=CCCCC1=O]

α-Iminone 2: 2-((2-((tert-butyldimethylsilyl)oxy)ethyl)amino)cyclohex-2-en-1-one General procedure E was applied. The corresponding epoxide precursor 7-oxabicyclo[4.1.0]heptan-2-one (1.0 g, 9 mmol) and 2-((tert-butyldimethylsilyl)oxy)ethan-1-amine (1.9 g, 10.8 mmol) were mixed in 9.0 mL of methanol, and 3.0 mL of water. The mixture was then refluxed for 4 h. After cooling, the solvent was removed and the residue was diluted with brine solution, extracted with EtOAc, dried (Na$_2$SO$_4$), filtered and concentrated in vacuo. The crude product was purified by flash chromatography (Silica gel, 20/80% EtOAc/hexane) to yield the desired product in 44% yield (1.1 g) as yellow liquid. $^1$H NM R (300 MHz, CDCl3): δ 5.43 (t, J=4.7 Hz, 1H), 4.44 (s, 1H), 3.73 (t, J=5.5 Hz, 2H), 2.92 (t, J=5.5 Hz, 2H), 2.49-2.38 (m, 2H), 2.33 (q, J=5.6 Hz, 2H), 1.91 (p, J=6.1 Hz, 2H), 0.86 (s, 9H), 0.02 (s, 6H). $^{13}$C NM R (75 MHz, CDCl3): δ 195.63, 145.98, 140.64, 111.26, 61.29, 45.14, 37.92, 25.86, 24.50, 23.46, 18.26, −5.39. IR (neat): 2928, 2856, 1675, 1629, 1472, 1629, 1472, 1252, 1101, 830, 775 cm$^{-1}$. HRMS (m/z) calcd. for C$_{14}$H$_{27}$NO$_2$ ([M+H]$^+$): 270.1884; found: 270.1887.

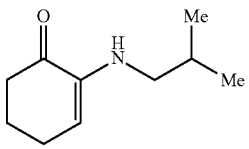 [SMILES: CC(C)CNC1=CCCCC1=O]

α-Iminone 3: 2-(isobutylamino)cyclohex-2-en-1-one General procedure E was applied. The corresponding epoxide precursor 7-oxabicyclo[4.1.0]heptan-2-one (1.0 g, 9.0 mmol) and 2-methylpropan-1-amine (988 mg, 13.5 mmol) were mixed in 9.0 mL of methanol, and 3.0 mL of water. The mixture was then refluxed for 4 h. After cooling, the solvent was removed and the residue was diluted with brine solution, extracted with EtOAc, dried (Na$_2$SO$_4$), filtered and concentrated in vacuo. The crude product was purified by flash chromatography (Silica gel, 8/92% ether/hexane) to yield the desired product in 74% yield (1.1 g) as light brown liquid. $^1$H NMR (300 MHz, CDCl3): δ 5.35 (t, J=4.7 Hz, 1H), 4.15 (s, 1H), 2.64-2.55 (m, 2H), 2.46-2.37 (m, 2H), 2.32 (q, J=5.6 Hz, 2H), 1.89 (p, J=6.1 Hz, 2H), 1.81-1.72 (m, 1H), 0.89 (d, J=6.7, 6H). $^{13}$C NMR (75 MHz, CDCl$_3$): δ

195.83, 140.68, 110.49, 51.09, 37.92, 27.60, 24.50, 23.48, 20.59. IR (neat): 3403, 2953, 2868, 2827, 1671, 1626, 1488, 1333, 1201, 1167, 1126, 866 cm$^{-1}$. HRMS (m/z) calcd. for C$_{10}$H$_{17}$NO ([M+H]$^+$): 168.1383; found: 168.1388.

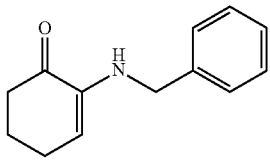 [SMILES: O=C1CCCC=C1NCc1ccccc1]

α-Iminone 4: 2-(benzylamino)cyclohex-2-en-1-one General procedure E was applied. The corresponding epoxide precursor 7-oxabicyclo[4.1.0]heptan-2-one (900 mg, 8.0 mmol) and benzylamine (1.71 g, 16.0 mmol) were mixed in 8.0 mL of methanol, and 2.3 mL of water. The mixture was then refluxed for 4 h. After cooling, the solvent was removed and the residue was diluted with saturated brine solution, extracted with EtOAc, dried (Na$_2$SO$_4$), filtered and concentrated in vacuo. The crude product was purified by flash chromatography (Silica gel, 20/80% EtOAc/hexane) to yield the desired product in 32% yield (1.02 g) as pale green solid (M.p. 56-59 éC). $^1$H NMR (300 MHz, CDCl$_3$): δ 7.20-7.36 (m, 5H), 5.42 (t, J=4.7 Hz, 1H), 4.60 (s, 1H), 4.08 (d, J=4.3 Hz, 2H), 2.59-2.41 (m, 2H), 2.33 (q, J=5.6 Hz, 2H), 1.94 (p, J=6.3 Hz, 2H). $^{13}$C NMR (75 MHz, CDCl3): δ 195.83, 140.35, 139.00, 128.50, 127.38, 127.08, 111.76, 47.55, 37.91, 24.48, 23.47. IR (neat): 3407, 2928, 1659, 1619, 1488, 1361, 1208, 742, 700 cm$^{-1}$. HRMS (m/z) calcd. for C$_{13}$H$_{15}$NO ([M+H]$^+$): 202.1226; found: 202.1224.

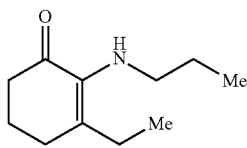 [SMILES: CCCNC1=C(CC)CCCC1=O]

α-Iminone 5: 3-ethyl-2-(propylamino)cyclohex-2-en-1-one General procedure E was applied. The corresponding epoxide precursor 6-Ethyl-7-oxabicyclo[4.1.0]heptan-2-one (1.42 g, 10.1 mmol) and propylamine (0.89 g, 15.2 mmol) were mixed in 10.0 mL of methanol, and 3.3 mL of water. The mixture was then refluxed for 4 h. After cooling, the solvent was removed and the residue was diluted with saturated brine solution, extracted with EtOAc, dried (Na$_2$SO$_4$), filtered and concentrated in vacuo. The crude product was purified by flash chromatography (Silica gel, 10/90% EtOAc/hexane) to yield the desired product in 48% yield (880 mg) as yellow liquid. $^1$H NMR (300 MHz, CDCl$_3$): δ 3.69 (s, 1H), 2.64 (t, J=7.1 Hz, 2H), 2.38-2.15 (m, 6H), 1.87-1.69 (m, 2H), 1.39 (q, J=7.3 Hz, 2H), 1.01 (t, J=7.6 Hz, 3H), 0.82 (t, J=7.4 Hz, 3H). $^{13}$C NMR (75 MHz, CDCl$_3$): δ 196.63, 143.41, 139.51, 51.27, 37.09, 28.93, 26.19, 23.56, 22.11, 11.59, 11.48. IR (neat): 3337, 2960, 2874, 1662, 1625, 1486, 1168 cm$^{-1}$. HRMS (m/z) calcd. for C$_{11}$H$_{19}$NO ([M+H]$^+$): 182.1539; found: 182.1539.

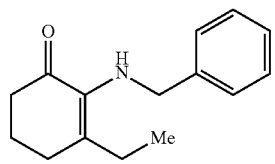 [SMILES: CCC1=C(NCc2ccccc2)C(=O)CCC1]

α-Iminone 6: 2-(benzylamino)-3-ethylcyclohex-2-en-1-one General procedure E was applied. The corresponding epoxide precursor 6-Ethyl-7-oxabicyclo[4.1.0]heptan-2-one (2.1 g, 15.0 mmol) and of benzylamine (2.4 g, 22.5 mmol) were mixed in 15.0 mL of methanol, and 5.0 mL of water. The mixture was then refluxed for 4 h. After cooling, the solvent was removed and the residue was diluted with saturated brine solution, extracted with EtOAc, dried (Na$_2$SO$_4$), filtered and concentrated in vacuo. The crude product was purified by flash chromatography (Silica gel, 10/90% EtOAc/hexane) to yield the desired product in 58% yield (1.99 g) as yellow liquid. $^1$H NMR (300 MHz, CDCl$_3$): δ 7.30 (d, J=4.3 Hz, 4H), 7.27-7.19 (m, 1H), 4.14 (s, 1H), 3.95 (s, 2H), 2.29-2.45 (m, 7H), 1.96-1.76 (m, 2H), 1.11 (t, J=7.5 Hz, 3H). $^{13}$C NMR (75 MHz, CDCl$_3$): δ 196.96, 140.98, 138.80, 128.91, 128.10, 128.03, 127.09, 48.34, 37.20, 32.04, 23.02, 22.34, 11.28. IR (neat): 2965, 2935, 2875, 1660, 1624, 1453, 1184, 1161, 734, 697 cm$^{-1}$. HRMS (m/z) calcd. for C$_{15}$H$_{19}$NO ([M+H]$^+$): 252.1364; found: 252.1357.

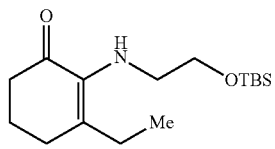 [SMILES: CCC1=C(NCCO[Si](C)(C)C(C)(C)C)C(=O)CCC1]

α-Iminone 7: 2-((2-((tert-butyldimethylsilyl)oxy)ethyl)amino)-3-ethylcyclohex-2-en-1-one General procedure E was applied. The corresponding epoxide precursor 6-ethyl-7-oxabicyclo[4.1.0]heptan-2-one (1.3 g, 9.4 mmol) and 2-((tert-butyldimethylsilyl)oxy)ethan-1-amine (2.46 g, 14.1 mmol) were mixed in 9.0 mL of methanol, and 3.0 mL of water. The mixture was then refluxed for 4 h. After cooling, the solvent was removed and the residue was diluted with saturated brine solution, extracted with EtOAc, dried (Na$_2$SO$_4$), filtered and concentrated in vacuo. The crude product was purified by flash chromatography (Silica gel, 1:1 DCM/hexane) to yield the desired product in 41% yield (1.17 g) as yellow oil. $^1$H NMR (300 MHz, CDCl$_3$): δ 3.68 (t, J=5.6 Hz, 2H), 2.91 (t, J=5.6 Hz, 2H), 2.48-2.24 (m, 6H), 1.91 (q, J=6.3 Hz, 2H), 1.10 (t, J=7.5 Hz, 3H), 0.91 (d, J=2.2 Hz, 9H), 0.06 (d, J=2.1 Hz, 6H). 13C NMR (75 MHz, CDCl$_3$): δ 196.41, 143.40, 139.35, 62.49, 51.01, 37.35, 29.10, 26.16, 25.89, 22.20, 18.28, 11.70, -5.36. IR (neat): 2952, 2928, 2856, 1666, 1627, 1462, 1253, 1103, 830, 774 cm$^{-1}$. HRMS (m/z) calcd. for C$_{16}$H$_{31}$NO$_2$Si ([M+H]$^+$): 298.2197; found: 298.2196.

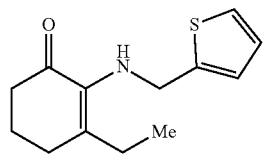 [SMILES: CCC1=C(NCc2cccs2)C(=O)CCC1]

α-Iminone 8: 3-ethyl-2-((thiophen-2-ylmethyl)amino)cyclohex-2-en-1-one General procedure E was applied. The corresponding epoxide precursor 6-ethyl-7-oxabicyclo[4.1.0]heptan-2-one (1.4 g, 10.0 mmol) and thiophen-2-ylmethanamine (1.7 g 15.0 mmol) were mixed in 10.0 mL of methanol, and 3.3 mL of water. The mixture was then refluxed for 4 h. After cooling, the solvent was removed and the residue was diluted with saturated brine solution, extracted with EtOAc, dried ($Na_2SO_4$), filtered and concentrated in vacuo. The crude product was purified by flash chromatography (Silica gel, 60/40% DCM/hexane) to yield the desired product in 48% yield (1.13 g) as yellow liquid. $^1$H NMR (300 MHz, $CDCl_3$): δ 7.15 (dd, J=4.9, 1.5 Hz, 1H), 6.97-6.80 (m, 2H), 4.18 (s, 1H), 4.12 (s, 2H), 2.39 (q, J=7.0 Hz, 6H), 1.87 (p, J=6.3 Hz, 2H), 1.11 (t, J=7.6 Hz, 3H). $^{13}$C NMR (75 MHz, $CDCl_3$): δ 196.45, 145.79, 143.37, 138.63, 126.58, 124.86, 124.34, 47.72, 37.18, 29.00, 26.27, 22.07, 11.63. IR (neat): 3319, 2930, 2872, 1656, 1619, 1464, 1160, 697 $cm^{-1}$. HRMS (m/z) calcd. for $C_{13}H_{17}NOS$ ($[M+Na]^+$): 258.0923; found: 258.0923.

α-Iminone 10: 4'-chloro-2-(propylamino)-5,6-dihydro-[1,1'-biphenyl]-3(4H)-one General procedure E was applied. The corresponding epoxide precursor 6-(4-chlorophenyl)-7-oxabicyclo[4.1.0]heptan-2-one (1.59 g, 7.15 mmol) and propylamine (610 mg, 10.7 mmol) in 7.5 mL of methanol, and 2.5 mL of water. The mixture was then refluxed for 4 h. After cooling, the solvent was removed and the residue was diluted with saturated brine solution, extracted with EtOAc, dried ($Na_2SO_4$), filtered and concentrated in vacuo. The crude product was purified by flash chromatography (Silica gel, 10/90% EtOAc/hexane) to yield the desired product in 66% yield (1.24 g) as orange paste. $^1$H NMR (300 MHz, $CDCl_3$): δ 7.37 (d, J=8.6 Hz, 2H), 7.33-7.25 (m, 2H), 4.28 (s, 1H), 2.64 (t, J=6.0 Hz, 2H), 2.57-2.44 (m, 2H), 2.32 (t, J=6.9 Hz, 2H), 2.01 (p, J=6.4 Hz, 2H), 1.28 (h, J=7.1 Hz, 2H), 0.71 (t, J=7.4 Hz, 3H). $^{13}$C NMR (75 MHz, $CDCl_3$): δ 196.76, 139.35, 139.10, 132.58, 129.50, 128.26, 126.75, 48.54, 37.06, 31.69, 23.05, 22.16, 11.32. IR (neat): 3351, 2956, 2927, 2873, 1662, 1608, 1488, 1191, 1091, 1016, 217, 691 $cm^{-1}$. HRMS (m/z) calcd. for $C_{15}H_{18}ClNO$ ($[M+Na]^+$): 286.0969; found: 286.0981.

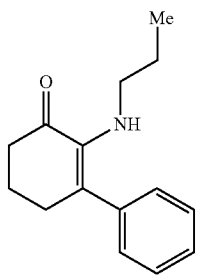 [SMILES: CCCNC1=C(c2ccccc2)CCCC1=O]

α-Iminone 9: 2-(propylamino)-5,6-dihydro-[1,1'-biphenyl]-3(4H)-one General procedure E was applied. The corresponding epoxide precursor 6-Phenyl-7-oxabicyclo[4.1.0]heptan-2-one (1.2 g, 6.3 mmol) and propylamine (560 mg, 9.5 mmol) were mixed in 6.0 mL of methanol, and 2.0 mL of water. The mixture was then refluxed for 4 h. After cooling, the solvent was removed and the residue was diluted with saturated brine solution, extracted with EtOAc, dried ($Na_2SO_4$), filtered and concentrated in vacuo. The crude product was purified by flash chromatography (Silica gel, 10/90% EtOAc/hexane) to yield the desired product in 48% yield (630 mg) as yellow liquid. $^1$H NMR (300 MHz, $CDCl_3$): δ 7.44-7.39 (m, 2H), 7.33 (t, J=7.7 Hz, 2H), 7.26-7.19 (m, 1H), 4.27 (s, 1H), 2.67 (t, J=6.0 Hz, 2H), 2.58-2.46 (m, 2H), 2.32 (t, J=7.0 Hz, 2H), 2.03 (q, J=6.4 Hz, 2H), 1.27 (h, J=7.2 Hz, 2H), 0.69 (t, J=7.4 Hz, 3H). $^{13}$C NMR (75 MHz, $CDCl_3$): δ 196.96, 140.97, 138.80, 128.89, 128.12, 128.04, 127.10, 48.34, 37.20, 32.04, 23.02, 22.34, 11.31. IR (neat): 3341, 2956, 2920, 2859, 1660, 1468, 1328, 1187, 1128, 765, 670 $cm^{-1}$. HRMS (m/z) calcd. for $C_{15}H_{19}NO$ ($[M+H]^+$): 230.1538; found: 230.1539.

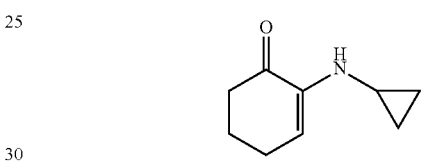

α-Iminone 11: 2-(cyclopropylamino)cyclohex-2-en-1-one General procedure E was applied. The corresponding epoxide precursor 7-oxabicyclo[4.1.0]heptan-2-one (1.12 g, 10.0 mmol) and propylamine (885 mg, 15.0 mmol) were mixed in 10.0 mL of methanol, and 3.3 mL of water. The mixture was then refluxed for 4 h. After cooling, the solvent was removed and the residue was diluted with brine solution, extracted with EtOAc, dried ($Na_2SO_4$), filtered and concentrated in vacuo. The crude product was purified by flash chromatography (Silica gel, 5/95% EtOAc/hexane) to yield 2-(cyclopropylamino)cyclohex-2-en-1-one in 80% yield (1.2 g) as yellow liquid. $^1$H NMR (300 MHz, $CDCl_3$): δ 5.83 (t, J=4.7 Hz, 1H), 4.46 (s, 1H), 2.46-2.32 (m, 4H), 2.12-2.03 (m, 1H), 1.92 (p, J=6.2 Hz, 2H), 0.61-0.52 (m, 2H), 0.40-0.31 (m, 2H). $^{13}$C NMR (75 MHz, $CDCl_3$): δ 195.83, 140.97, 113.19, 37.86, 24.54, 24.27, 23.52, 6.53. IR (neat): 3394, 2940, 2839, 1672, 1630, 1481, 1379 $cm^{-1}$. HRMS (m/z) calcd. for $C_9H_{13}NO$ ($[M+H]^+$): 152.1070; found: 152.1070.

7. General Procedure F: Synthesis of Stable α-Enaminones

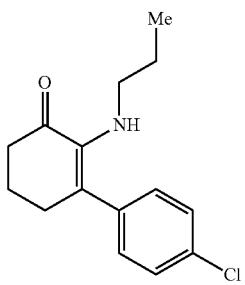 [SMILES: CCCNC1=C(c2ccc(Cl)cc2)CCCC1=O]

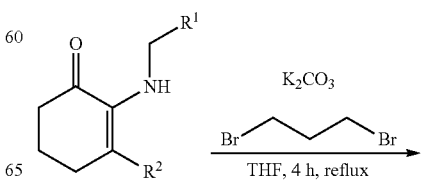

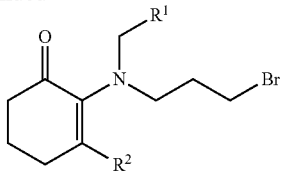

According to Sinha et al.[3] To a stirred solution of amine (1.0 equiv.) in THF (1M) was added anhydrous K₂CO₃ (2 equiv.) followed by dibromopropane (10.0 equiv.) at room temperature and the resultant mixture was refluxed for 16 h. The crude mixture was then filtered and concentrated in vacuo and purified by flash chromatography to yield the desired product.

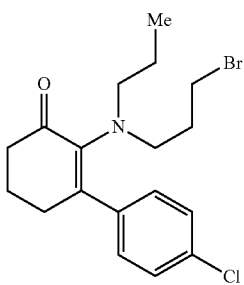 [SMILES: CCCN(CCCBr)C1=C(c2ccc(Cl)cc2)CCCC1=O]

α-Enaminone 1: 2-((3-bromopropyl)(propyl)amino)-4'-chloro-5,6-dihydro-[1,1'-biphenyl]-3(4H)-one General procedure F was applied. α-Iminone (10) (1.0 g, 3.8 mmol) prepared according to General Procedure E, anhydrous K₂CO₃ (1.05 g, 7.6 mmol), dibromopropane (7.6 g, 38.0 mmol) were mixed in THF (4.0 mL). The resultant mixture was refluxed for 16 h. After cooling, the reaction mixture was filtered and concentrated in vacuo. The crude mixture was purified by flash chromatography (Silica gel, 8/92% EtOAc/hexane) to yield the desired product in 54% yield (800 mg) as yellow liquid ¹H NMR (300 MHz, CDCl₃): δ 7.33 (d, J=8.3 Hz, 2H), 7.24 (d, J=8.3 Hz, 2H), 3.11 (t, J=6.6 Hz, 2H), 2.80 (t, J=6.7 Hz, 2H), 2.61-2.73 (m, 4H), 2.51 (t, 2H), 2.04 (p, J=6.5 Hz, 2H), 1.72 (p, J=6.7 Hz, 2H), 1.35-1.14 (m, 2H), 0.72 (t, J=7.4 Hz, 3H). ¹³C NMR (75 MHz, CDCl3): δ 199.29, 151.65, 142.34, 139.11, 133.49, 129.10, 128.12, 55.47, 51.27, 39.63, 32.69, 32.06, 31.84, 22.39, 21.75, 11.60. IR (neat): 2956, 2930, 2869, 1670, 1489, 1091, 1016, 823, 699 cm⁻¹. HRMS (m/z) calcd. for C₁₈H₂₃BrClNO ([M+Na]⁺): 408.0524; found: 408.0523.

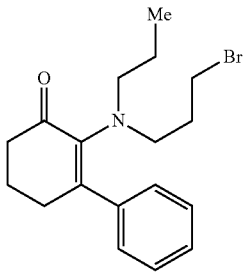 [SMILES: CCCN(CCCBr)C1=C(c2ccccc2)CCCC1=O]

α-Enaminone 2: 2-((3-bromopropyl)(propyl)amino)-5,6-dihydro-[1,1'-biphenyl]-3(4H)-one General procedure F was applied. α-Iminone (9) (600 mg, 2.62 mmol) prepared according to General Procedure E, anhydrous K₂CO₃ (725 mg, 5.24 mmol), dibromopropane (5.3 g, 26.0 mmol) were mixed in THF (2.6 mL). The resultant mixture was refluxed for 16 h. After cooling, the reaction mixture was filtered and concentrated in vacuo. The crude mixture was purified by flash chromatography (Silica gel, 20/80% Ether/hexane) to yield the desired product in 81% yield (730 mg) as yellow oil. ¹H NMR (300 MHz, CDCl₃): δ 7.43-7.17 (m, 5H), 3.01 (t, J=6.6 Hz, 2H), 2.78 (t, J=6.6 Hz, 2H), 2.69 (td, J=6.8, 6.1, 3.9 Hz, 4H), 2.50 (dd, J=7.5, 5.9 Hz, 2H), 2.08-1.98 (m, 2H), 1.69 (p, J=6.6 Hz, 2H), 1.30-1.23 (m, 2H), 0.71 (t, J=7.3 Hz, 3H). ¹³C NMR (75 MHz, CDCl₃): δ 199.51, 153.62, 142.02, 140.75, 127.88, 127.59, 55.66, 51.18, 39.69, 32.97, 32.21, 31.95, 22.49, 21.76, 11.61. IR (neat): 2955, 2927, 2869, 1667, 1449, 1180, 1116, 753, 697 cm⁻¹. HRMS (m/z) calcd. for C₁₈H₂₄BrNO ([M+Na]⁺): 372.0933; found: 372.0931.

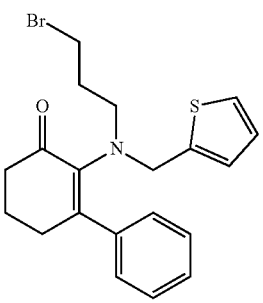 [SMILES: O=C1CCCC(c2ccccc2)=C1N(CCCBr)Cc1cccs1]

α-Enaminone 13: 2-((3-bromopropyl)(thiophen-2-ylmethyl)amino)-5,6-dihydro-[1,1'-biphenyl]-3(4H)-one General procedure F was applied. The corresponding α-iminone 2-((thiophen-2-ylmethyl)amino)-5,6-dihydro-[1,1'-biphenyl]-3(4H)-one (982 mg, 3.47 mmol), anhydrous K₂CO₃ (994 mg, 6.94 mmol), dibromopropane (7 g, 34.7 mmol) were mixed in THF (3.5 mL). The resultant mixture was refluxed for 16 h. After cooling, the reaction mixture was filtered and concentrated in vacuo. The crude mixture was purified by flash chromatography (Silica gel, 1:1 DCM/hexane) to yield the desired product in 16% yield (218 mg) as pale yellow solid (M.p. 72-75 éC). ¹H NMR (300 MHz, CDCl₃): δ 7.43-7.29 (m, 3H), 7.22-7.12 (m, 3H), 6.90-6.82 (m, 1H), 6.81-6.76 (m, 1H), 4.24 (s, 2H), 2.90 (t, J=6.9 Hz, 2H), 2.79 (t, J=6.5 Hz, 2H), 2.71 (t, J=6.0 Hz, 2H), 2.59-2.51 (m, 2H), 2.06 (p, J=6.2 Hz, 2H), 1.64 (p, J=6.8 Hz, 3H). ¹³C NMR (75 MHz, CDCl₃): δ 199.27, 155.96, 143.19, 141.11, 140.27, 128.14, 127.93, 127.47, 126.15, 124.95, 53.01, 50.10, 39.66, 33.20, 32.05, 31.86, 22.41. IR (neat): 2951, 2926, 2850, 1662, 1610, 1211, 755, 698 cm⁻¹.

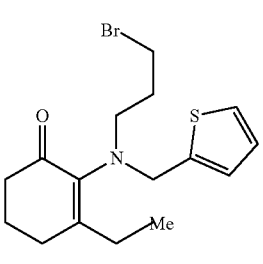 [SMILES: CCC1=C(N(CCCBr)Cc2cccs2)C(=O)CCC1]

α-Enaminone 4: 2-((3-bromopropyl)(thiophen-2-ylmethyl)amino)-3-ethylcyclohex-2-en-1-one General procedure F was applied. α-Iminone (8) (705 mg, 3.0 mmol) prepared according to General Procedure E, anhydrous K₂CO₃ (830 mg, 6.0 mmol), dibromopropane (6.1 g, 30.0 mmol) were mixed in THF (3.0 mL). The resultant mixture was refluxed for 16 h. After cooling, the reaction mixture was filtered and concentrated in vacuo. The crude mixture was purified by flash chromatography (Silica gel, 10/90% EtOAc/hexane) to yield the desired product in 50% yield (543 mg) as yellow oil. $^1$H NMR (300 MHz, CDCl$_3$): δ 7.17 (dd, J=5.1, 1.3 Hz, 1H), 6.85-6.91 (m, 1H), 6.91-6.80 (m, 1H), 4.19 (s, 2H), 3.35 (t, J=6.9 Hz, 2H), 3.01 (t, J=7.0 Hz, 2H), 2.51 (q, J=9.5, 8.6 Hz, 2H), 2.36 (dt, J=8.9, 6.4 Hz, 4H), 1.86 (dp, J=13.9, 6.7 Hz, 4H), 0.97 (t, J=7.6 Hz, 3H). $^{13}$C NMR (75 MHz, CDCl$_3$): δ 198.33, 164.15, 144.40, 140.48, 126.29, 125.57, 124.64, 53.63, 51.27, 39.63, 32.43, 31.81, 29.33, 26.44, 22.33, 11.96. IR (neat): 2924, 2861, 1667, 1129, 910, 729, 702 cm$^{-1}$. HRMS (m/z) calcd. for C$_{16}$H$_{22}$BrNOS ([M+Na]$^+$): 378.0498; found: 378.0495.

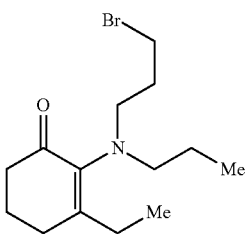 [SMILES: CCCN(CCCBr)C1=C(CC)CCCC1=O]

α-Enaminone 5: 2-((3-bromopropyl)(propyl)amino)-3-ethylcyclohex-2-en-1-one General procedure F was applied. α-Iminone (5) (740 mg, 4.0 mmol) prepared according to General Procedure E, anhydrous K$_2$CO$_3$ (1.1 g, 8.0 mmol), dibromopropane (8.28 g, 40.0 mmol) were mixed in THF (4.0 mL). The resultant mixture was refluxed for 16 h. After cooling, the reaction mixture was filtered and concentrated in vacuo. The crude mixture was purified by flash chromatography (Silica gel, 10/90% ether/hexane) to yield the desired product in 69% yield (857 mg) as yellow oil. $^1$H NMR (300 MHz, CDCl$_3$): δ 3.39 (t, J=6.8 Hz, 2H), 2.94 (t, J=6.9 Hz, 2H), 2.79-2.67 (m, 2H), 2.49 (q, J=7.6 Hz, 2H), 2.29-2.40 (m, 4H), 1.85 (dp, J=13.6, 6.5 Hz, 4H), 1.28 (dq, J=15.4, 7.7 Hz, 2H), 1.01 (t, J=7.6 Hz, 3H), 0.80 (t, J=7.3 Hz, 3H). $^{13}$C NMR (75 MHz, CDCl$_3$): δ 198.37, 162.82, 141.08, 56.40, 52.25, 39.79, 32.62, 32.09, 29.24, 26.19, 22.44, 22.41, 11.95, 11.79. IR (neat): 2957, 2933, 2870, 1667, 1611, 1457, 1218, 1117, 776 cm$^{-1}$. HRMS (m/z) calcd. for C$_{14}$H$_{24}$BrNO ([M+H]$^+$): 302.1114; found: 302.1113.

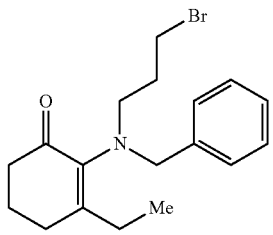 [SMILES: CCC1=C(N(CCCBr)Cc2ccccc2)C(=O)CCC1]

α-Enaminone 6: 2-(benzyl(3-bromopropyl)amino)-3-ethylcyclohex-2-en-1-one General procedure F was applied. α-Iminone (6) (1.2 g, 5.24 mmol) prepared according to General Procedure E, o anhydrous K$_2$CO$_3$ (1.45 g, 10.48 mmol), dibromopropane (10.6 g, 52.0 mmol) were mixed in THF (5.0 mL). The resultant mixture was refluxed for 16 h. After cooling, the reaction mixture was filtered and concentrated in vacuo. The crude mixture was purified by flash chromatography (Silica gel, 15/85% ether/hexane) to yield enaminone in 70% yield (1.26 g) as yellow oil. $^1$H NMR (300 MHz, CDCl$_3$): δ 7.36-7.13 (m, 5H), 4.00 (s, 2H), 3.35 (t, J=6.9 Hz, 2H), 3.01 (t, J=7.0 Hz, 2H), 2.32-2.45 (m, 4H), 2.27 (t, J=6.1 Hz, 2H), 1.92-1.77 (m, 4H), 0.85 (t, J=7.6 Hz, 3H). $^{13}$C NMR (75 MHz, CDCl$_3$): δ 198.50, 163.57, 140.47, 139.93, 129.12, 128.01, 126.77, 58.64, 51.81, 39.73, 32.46, 31.81, 29.19, 26.22, 22.31, 11.66. IR (neat): 2959, 2935, 2863, 1664, 1610, 1453, 1130, 728, 699 cm$^{-1}$. HRMS (m/z) calcd. for C$_{18}$H$_{24}$BrNO ([M+Na]$^+$): 372.0934; found: 372.0940.

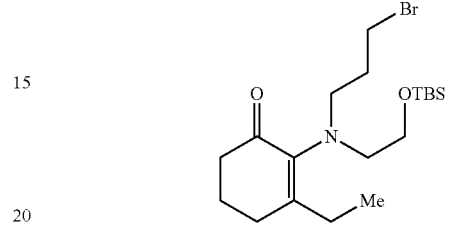

α-Enaminone 7: 2-((3-bromopropyl)(2-((tert-butyldimethylsilyl)oxy)ethyl)amino)-3-ethyl-cyclohex-2-en-1-one General procedure F was applied. α-Iminone (7) (1.17 g, 3.84 mmol) prepared according to General Procedure E, anhydrous K$_2$CO$_3$ (1.06 g, 7.7 mmol), dibromopropane (7.95 g, 38.4 mmol) and THF (4.0 mL). The resultant mixture was refluxed for 16 h. After cooling, the reaction mixture was filtered and concentrated in vacuo. The crude mixture was purified by flash chromatography (Silica gel, 10/90% ether/hexane) to yield enaminone in 83% yield (946 mg) as pale yellow liquid. $^1$H NMR (300 MHz, CDCl$_3$): δ 3.52 (t, J=6.4 Hz, 2H), 3.45 (t, J=6.7 Hz, 2H), 2.96 (dt, J=19.0, 6.6 Hz, 4H), 2.54 (q, J=7.7 Hz, 2H), 2.38 (t, J=6.4 Hz, 4H), 1.88 (dp, J=13.7, 6.6 Hz, 4H), 1.04 (t, J=7.6 Hz, 3H), 0.87 (s, 9H), 0.03 (s, 6H). $^{13}$C NMR (75 MHz, CDCl$_3$): δ 198.14, 162.96, 141.38, 62.27, 56.84, 52.64, 39.68, 32.77, 32.07, 29.22, 26.13, 25.92, 22.40, 18.29, 11.99, −5.31. IR (neat): 2952, 2928, 2855, 1670, 1462, 1255, 1099, 939, 832, 774 cm$^{-1}$. HRMS (m/z) calcd. for C$_{19}$H$_{36}$BrNO$_2$SiNa ([M+Na]$^+$): 252.1466; found: 252.1357.

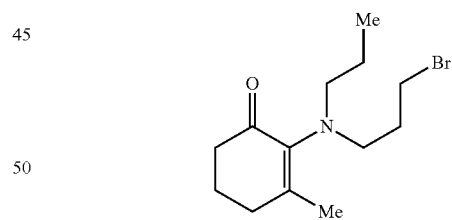

α-Enaminone 8: 2-((3-bromopropyl)(propyl)amino)-4'-chloro-5,6-dihydro-[1,1'-biphenyl]-3(4H)-one General procedure F was applied. The corresponding α-iminone 3-methyl-2-(propylamino)cyclohex-2-en-1-one (330 mg, 1.98 mmol), anhydrous K$_2$CO$_3$ (545 mg, 3.96 mmol), dibromopropane (3.87 g, 19.8 mmol) were mixed in THF (2.0 mL). The resultant mixture was refluxed for 16 h. After cooling, the reaction mixture was filtered and concentrated in vacuo. The crude product was purified by flash chromatography (Silica gel, 10/90% EtOAc/hexane) to yield enaminone in 79% yield (448 mg) as yellow oil. $^1$H NMR (300 MHz, CDCl$_3$): δ 3.42 (t, J=6.8 Hz, 2H), 2.97 (t, J=6.8 Hz, 2H), 2.76 (t, J=7.6 Hz, 2H), 2.44-2.34 (m, 4H), 1.99 (s, 3H), 1.92-179 (m, 4H), 1.30 (h, J=7.8 Hz, 2H), 0.81 (t, J=7.4 Hz, 3H). $^{13}$C NMR (75 MHz, CDCl$_3$): δ 198.11, 157.72, 141.68, 56.19, 52.02, 39.76, 32.46, 32.37, 32.19, 22.29, 22.21, 20.51, 11.84. IR (neat): 2930, 2869, 1667, 1429, 1252, 1219, 1121 cm$^{-1}$. HRMS (m/z) calcd. for C$_{13}$H$_{22}$BrNO ([M+Na]$^+$): 310.0777; found: 310.0776.

8. General Procedure G:

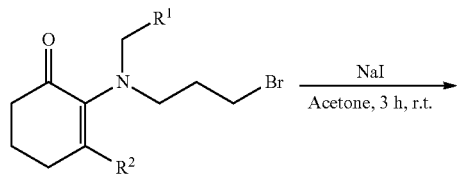

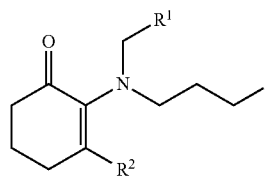

α-Enaminone (1.0 equiv.) and NaI (5.0 equiv.) were dissolved in acetone (0.5M). The solution was stirred for 3 h at room temperature. The suspension was filtered and the filtrate was concentrated in vacuo. The crude mixture was purified by flash chromatography to yield the desired product.$^4$

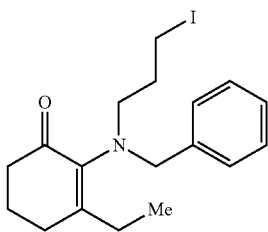 [SMILES: CCC1=C(N(CCCI)Cc2ccccc2)C(=O)CCC1]

α-Enaminone 9: 2-(benzyl(3-iodopropyl)amino)-3-ethylcyclohex-2-en-1-one General procedure G was applied. α-Enaminone (6) (1.05 g, 3.0 mmol) prepared according to General Procedure F and NaI (2.25 g, 15.0 mmol) were dissolved in acetone (6.0 mL). The solution was stirred for 3 h at room temperature. The suspension was filtered and the filtrate was concentrated in vacuo. The crude mixture was purified by flash chromatography (Silica gel, 15/85% ether/hexane) to yield iodo-enaminone in 89% yield (1.06 g) as yellow liquid $^1$H NMR (300 MHz, CDCl$_3$): δ 7.31-7.13 (m, 5H), 4.00 (s, 2H), 3.12 (t, J=7.1 Hz, 2H), 2.97 (t, J=7.0 Hz, 2H), 2.39 (dt, J=16.5, 7.3 Hz, 4H), 2.28 (t, J=6.1 Hz, 2H), 1.93-1.72 (m, 4H), 0.86 (t, J=7.7 Hz, 3H). $^{13}$C NMR δ 198.49, 163.55, 140.50, 139.94, 129.14, 128.03, 126.79, 58.71, 53.82, 39.74, 33.31, 29.20, 26.24, 22.33, 11.72, 4.55. IR (neat): 2935, 2863, 1664, 1453, 1193, 1131, 728, 699 cm$^{-1}$. HRMS (m/z) calcd. for C$_{18}$H$_{24}$INO ([M+Na]$^+$): 420.0795; found: 420.0794.

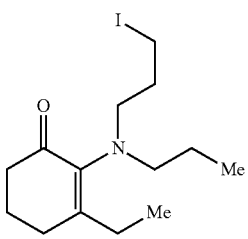 [SMILES: CCCN(CCCI)C1=C(CC)CCCC1=O]

α-Enaminone 10: 2-((3-iodopropyl)(propyl)amino)-3-ethylcyclohex-2-en-1-one General procedure G was applied, α-Enaminone (5) (602 mg, 2.0 mmol) prepared according to General Procedure F and NaI (1.50 g, 10.0 mmol) were dissolved in acetone (4.0 mL). The solution was stirred for 3 h at room temperature. The suspension was filtered and the filtrate was concentrated in vacuo. The crude mixture was purified by flash chromatography (Silica gel, 10/90% ether/hexane) to yield iodo-enaminone in 94% yield (660 mg) as yellow liquid. $^1$H NMR (300 MHz, CDCl$_3$): δ 3.15 (t, J=7.0 Hz, 2H), 2.88 (t, J=6.9 Hz, 2H), 2.73 (t, J=8.7, 6.7 Hz, 2H), 2.49 (q, J=7.6 Hz, 2H), 2.38-2.30 (m, 4H), 1.93-1.75 (m, 4H), 1.28 (h, J=7.8 Hz, 2H), 1.01 (t, J=7.6 Hz, 3H), 0.79 (t, J=7.3 Hz, 3H). $^{13}$C NM R (75 MHz, CDCl$_3$): δ 198.36, 162.76, 141.11, 56.50, 54.29, 39.78, 33.43, 29.24, 26.20, 22.46, 22.42, 12.00, 11.80, 4.99. IR (neat): 2956, 2932, 2870, 1667, 1456, 1200, 1172, 1115 cm$^{-1}$. HRMS (m/z) calcd. for C$_{14}$H$_{24}$INONa ([M+Na]$^+$): 372.0794; found: 372.0795.

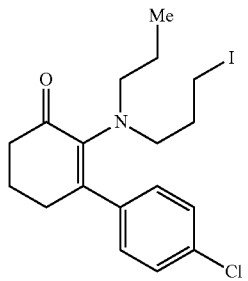 [SMILES: CCCN(CCCI)C1=C(c2ccc(Cl)cc2)CCCC1=O]

α-Enaminone 11: 2-((3-iodopropyl)(propyl)amino)-4'-chloro-5,6-dihydro-[1,1'-biphenyl]-3(4H)-one General procedure G was applied. α-Enaminone (1) (260 mg, 0.67 mmol) prepared according to General Procedure F and NaI (500 mg, 3.35 mmol) were dissolved in acetone (1.4 mL). The solution was stirred for 3 h at room temperature. The suspension was filtered and the filtrate was concentrated in vacuo. The crude mixture was purified by flash chromatography (Silica gel, 5/95% ether/hexane) to yield 2-((3-iodopropyl)(propyl)amino)-4'-chloro-5,6-dihydro-[1,1'-biphenyl]-3(4H)-one in 93% yield (269 mg) as yellow oil. $^1$H NMR (300 MHz, CDCl$_3$): δ 7.35 (d, J=8.7 Hz, 2H), 7.29-7.22 (m, 2H), 2.90 (t, J=6.8 Hz, 2H), 2.78-2.63 (m, 5H), 2.55-2.49 (m, 2H), 2.05 (p, J=6.3 Hz, 2H), 1.70 (p, J=6.8 Hz, 2H), 1.37-1.21 (m, 3H), 0.73 (t, J=7.4 Hz, 3H). $^{13}$C NMR (75 MHz, CDCl$_3$): δ 199.30, 151.34, 142.39, 139.11, 133.50, 129.10, 128.16, 55.49, 53.33, 39.63, 32.67, 22.39, 21.80, 11.61, 5.14. IR (neat): 2955, 2929, 2666, 1670, 1489, 1201, 1090, 822, 731 cm$^{-1}$. HRMS (m/z) calcd. for C$_{18}$H$_{23}$ClNO ([M+Na]$^+$): 454.0405; found: 454.0407.

Dimerization of α-Enaminone Precursor: Access to Carbazoledione

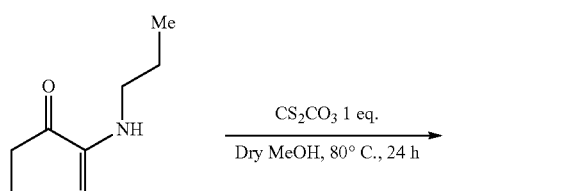

1

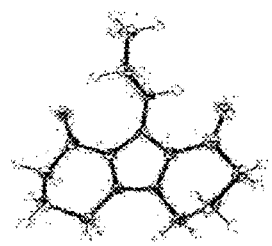

X-Ray crystal structure of 2

9-propyl-3,4,5,6,7,9-hexahydro-1H-carbazole-1,8-(2H)-dione 2-(propylamino)cyclohex-2-en-1-one 1 (0.9 g, 5.9 mmol, 1 equiv.) and Cs$_2$CO$_3$ (0.59 g, 1.8 mmol, 2 equiv.) were mixed in 10.0 mL of dry methanol. The mixture was then refluxed at 80° C. for 24 h. After cooling, the solvent was removed and the residue was diluted with saturated brine solution, extracted with EtOAc, dried (Na$_2$SO$_4$), filtered and concentrated in vacuo. The crude product was purified by flash chromatography (Silica gel, 10% ether/hexane) to yield 2 in 30% yield (220 mg) as colorless crystals. $^1$H NMR (300 MHz, Chloroform-d) δ 4.76-4.64 (m, 1H), 2.63 (t, J=6.1 Hz, 2H), 2.59-2.48 (m, 2H), 2.07 (h, J=6.3, 5.8 Hz, 2H), 1.77-1.58 (m, 1H), 0.88 (t, J=7.4 Hz, 1H). $^{13}$C NMR (75 MHz, cdcl3) δ 191.41, 131.56, 129.79, 47.97, 40.44, 24.72, 24.25, 21.77, 10.89.

Direct Synthesis of Dibenzoazepines from α-Enaminones

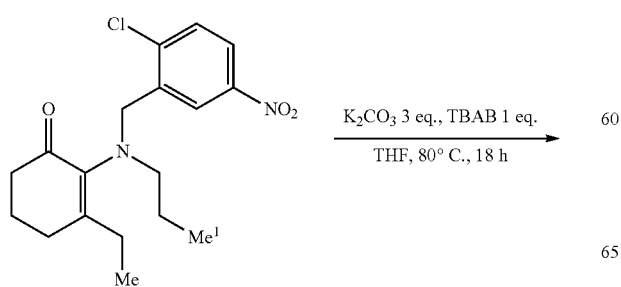

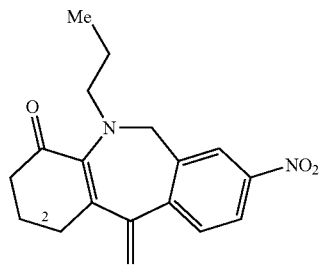

Starting enaminone 1 (70 mg, 0.2 mmol, 1 equiv.) and K$_2$CO$_3$ (80 mg, 0.6 mmol, 3 equiv.) were mixed in 0.5 mL of dry THF. The mixture was then refluxed at 80° C. for 18 h. After cooling, the solvent was removed and the residue was purified by flash chromatography (Silica gel, 10% ether/hexane) to yield 2. $^1$H NMR (300 MHz, Chloroform-d) δ 8.15 (d, J=10.9 Hz, 1H), 7.94 (s, 1H), 7.40 (d, J=8.4 Hz, 1H), 5.71 (s, 1H), 5.27 (s, 1H), 4.20 (s, 2H), 2.70 (t, J=6.2 Hz, 2H), 2.63-2.56 (m, 2H), 2.51-2.44 (m, 2H), 1.99 (p, J=6.4 Hz, 2H), 1.55 (h, J=7.4 Hz, 2H), 0.80 (t, J=7.4 Hz, 3H).

The invention claimed is:

1. A process for the preparation of a heterocyclic compound comprising the step of:

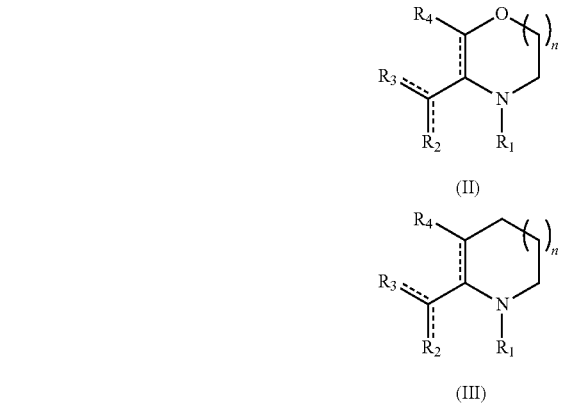

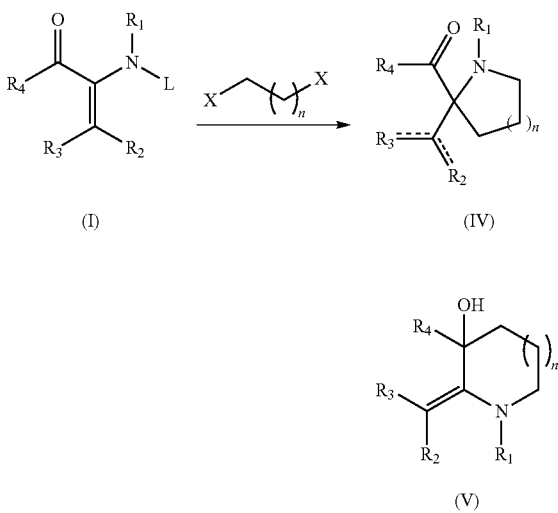

-continued

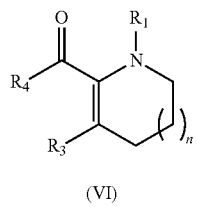

(VI)

Wherein

X is a halogen;

═══ is a single or double bond;

R1-R4 are each independently selected from H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(═O)($C_1$-$C_8$ alkyl), —C(═O)($C_1$-$C_8$ alkyl), —C(═O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; or $R_3$ and $R_4$ together with the atoms they are attached to form a 5 to 15 saturated, unsaturated or aromatic ring;

L is H;

n is an integer between 1 to 10;

And wherein

| When $R_2$ is | And n is | Main Product produces is/are |
|---|---|---|
| H | Greater than 1 | Compound (VI) |
| straight or branched $C_1$-$C_{15}$ alkyl, straight or branched $C_2$-$C_{15}$ alkenyl, straight or branched $C_2$-$C_{15}$ alkynyl, optionally substituted as above | Greater than 1 | Compound (IV) and Compound (V) |
|  | 1 | Compound (II) |
| $C_5$-$C_{12}$ aryl, $C_5$-$C_{12}$ heteroaryl; optionally substituted as above | Greater than 1 | Compound (III) and Compound (IV) |
|  | 1 | Compound (II). |

2. A process according to claim 1, wherein

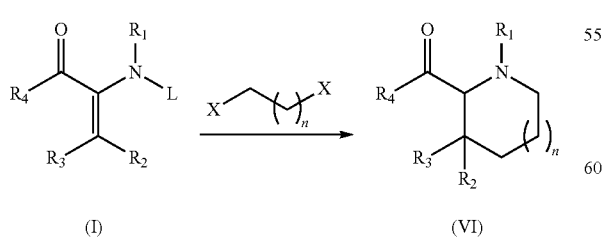

Wherein R2 is H and n is greater than 1.

3. A process according to claim 1, wherein

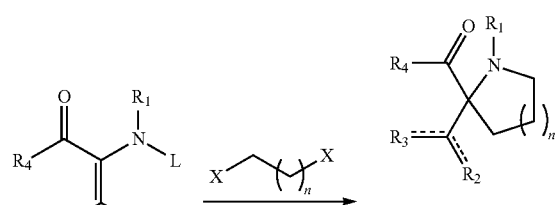

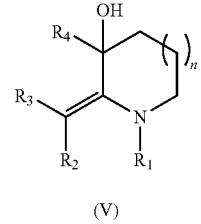

Wherein R2 is straight or branched $C_1$-$C_{15}$ alkyl, straight or branched $C_2$-$C_{15}$ alkenyl, straight or branched $C_2$-$C_{15}$ alkynyl, optionally substituted as defined above and n is greater than 1.

4. A process according to claim 1, wherein

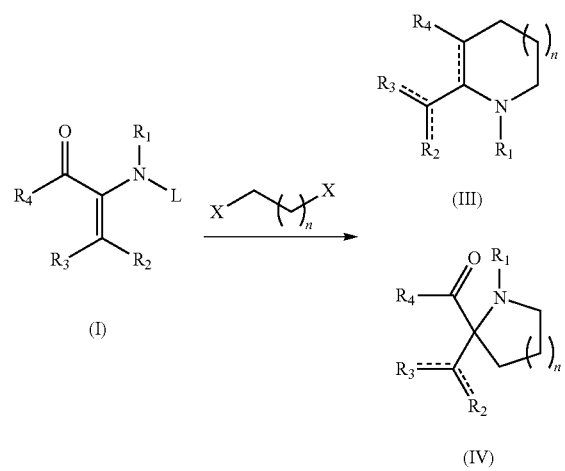

Wherein $R_2$ is $C_5$-$C_{12}$ aryl, $C_5$-$C_{12}$ heteroaryl; optionally substituted as above and n is greater than 1.

5. A process according to claim 1, wherein

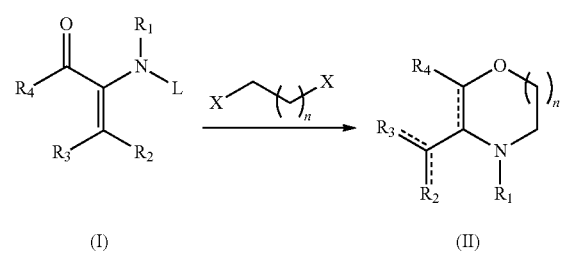

Wherein R2 is straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; and n is 1.

6. A process according to claim 1, wherein

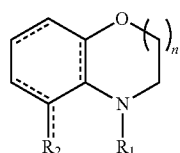

(VIII)

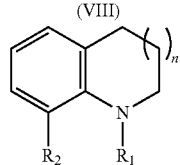

(IX)

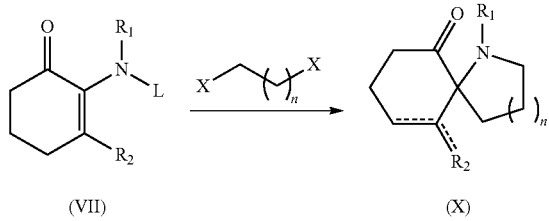

(VII)  (X)

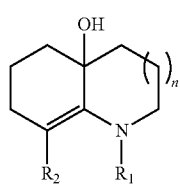

(XI)

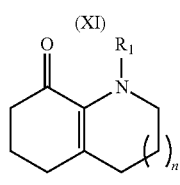

(XII)

Wherein
X is a halogen;
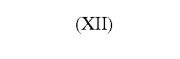 is a single or double bond;
R1-R4 are each independently selected from H, straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; or $R_3$ and $R_4$ together with the atoms they are attached to form a 5 to 15 saturated, unsaturated or aromatic ring;

L is H;

n is an integer between 1 to 10;

And wherein

| When $R_2$ is | And n is | Main Product produces is/are |
|---|---|---|
| H | Greater than 1 | Compound (XII) |
| straight or branched $C_1$-$C_{15}$ alkyl, straight or branched $C_2$-$C_{15}$ alkenyl, straight or branched $C_2$-$C_{15}$ alkynyl, optionally substituted as above | Greater than 1 | Compound (XI) and Compound (X) |
|  | 1 | Compound (VIII) |
| $C_5$-$C_{12}$ aryl, $C_5$-$C_{12}$ heteroaryl; optionally substituted as above | Greater than 1 | Compound (IX) and Compound (X) |
|  | 1 | Compound (VIII). |

7. A process according to claim 1, wherein

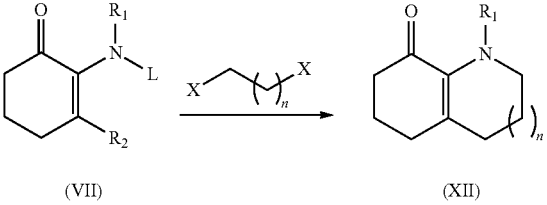

(VII)  (XII)

Wherein R2 is H and n is greater than 1.

8. A process according to claim 1, wherein

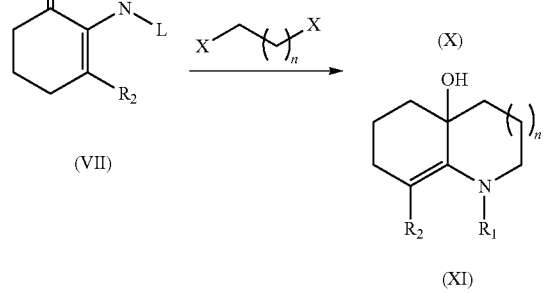

(VII)  (X)  (XI)

Wherein R2 is straight or branched $C_1$-$C_{15}$ alkyl, straight or branched $C_2$-$C_{15}$ alkenyl, straight or branched $C_2$-$C_{15}$ alkynyl, optionally substituted as defined above and n is greater than 1.

9. A process according to claim 1, wherein

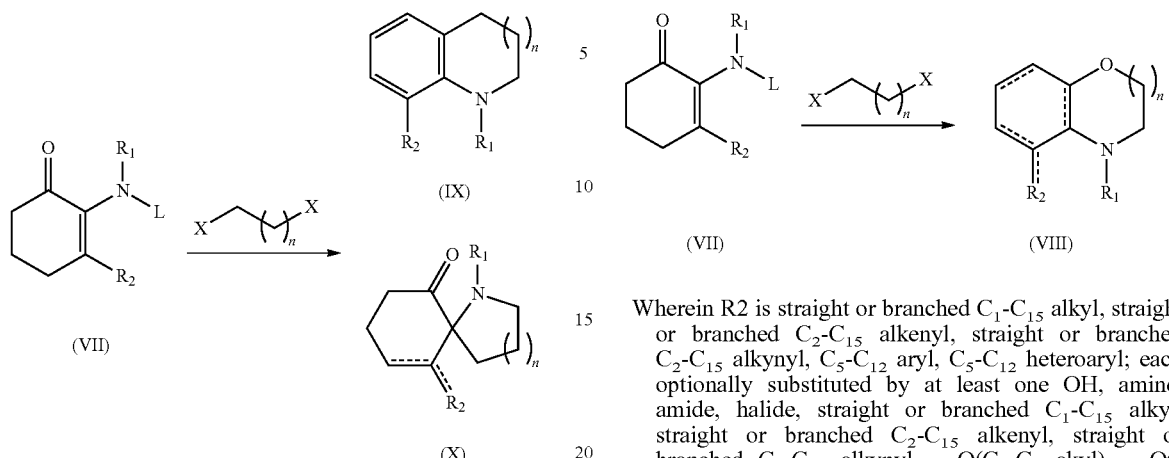

Wherein R2 is $C_5$-$C_{12}$ aryl, $C_5$-$C_{12}$ heteroaryl; optionally substituted as above and n is greater than 1.

10. A process according to claim 1, wherein

Wherein R2 is straight or branched $C_1$-$C_{15}$ alkyl, straight or branched $C_2$-$C_{15}$ alkenyl, straight or branched $C_2$-$C_{15}$ alkynyl, $C_5$-$C_{12}$ aryl, $C_5$-$C_{12}$ heteroaryl; each optionally substituted by at least one OH, amine, amide, halide, straight or branched $C_1$-$C_{15}$ alkyl, straight or branched $C_2$-$C_{15}$ alkenyl, straight or branched $C_2$-$C_{15}$ alkynyl, —O($C_1$-$C_8$ akyl), —OC(=O)($C_1$-$C_8$ alkyl), —C(=O)($C_1$-$C_8$ alkyl), —C(=O)O($C_1$-$C_8$ alkyl); $C_5$-$C_{12}$ aryl, $C_5$-$C_{12}$ heteroaryl, $C_3$-$C_{12}$ cycloalkyl, $C_3$-$C_{12}$ heterocycloalkyl; and n is 1.

* * * * *